US012390599B2

(12) United States Patent
Armiento et al.

(10) Patent No.: US 12,390,599 B2
(45) Date of Patent: Aug. 19, 2025

(54) ELECTRONIC POSITION SENSING SYSTEM, METHOD, AND APPARATUS

(71) Applicant: University of Massachusetts, Boston, MA (US)

(72) Inventors: Craig A. Armiento, Acton, MA (US); David Musoke, Lowell, MA (US); Alexander Z. Senckowski, Lowell, MA (US); Alkim Akyurtlu, Arlington, MA (US); Edward D. Kingsley, Stow, MA (US); Kyle M. Homan, Pembroke, MA (US)

(73) Assignee: University of Massachusetts, Boston, MA (US)

( * ) Notice: Subject to any disclaimer, the term of this patent is extended or adjusted under 35 U.S.C. 154(b) by 1287 days.

(21) Appl. No.: 17/117,842

(22) Filed: Dec. 10, 2020

(65) Prior Publication Data

US 2021/0146062 A1   May 20, 2021

Related U.S. Application Data

(63) Continuation of application No. PCT/US2019/036693, filed on Jun. 12, 2019.
(Continued)

(51) Int. Cl.
*A61M 5/315* (2006.01)
*A61B 5/06* (2006.01)

(52) U.S. Cl.
CPC ......... *A61M 5/31568* (2013.01); *A61B 5/065* (2013.01); *A61M 5/31551* (2013.01);
(Continued)

(58) Field of Classification Search
CPC .......... A61M 5/31568; A61M 5/31551; A61M 5/31585; A61M 2205/3317; A61B 5/065; A61B 2090/0811
See application file for complete search history.

(56) References Cited

U.S. PATENT DOCUMENTS

| | | | | | |
|---|---|---|---|---|---|
| 5,720,733 | A | * | 2/1998 | Brown | G01F 3/16 222/23 |
| 5,954,700 | A | * | 9/1999 | Kovelman | A61M 5/24 604/207 |

(Continued)

OTHER PUBLICATIONS

International Search Report, PCT/US2019/036693, Oct. 15, 2019, pp. 4.

*Primary Examiner* — Oommen Jacob
(74) *Attorney, Agent, or Firm* — Armis IP Law, LLC

(57) ABSTRACT

A position tracking system includes a member extending along a lengthwise axis. Multiple position tracking elements (such as conductive strips) are fabricated to be exposed on a surface of the member. The multiple position tracking elements form a sequence along the lengthwise axis and are spaced apart from each other. The position tracking system further includes a probe. The probe monitors for presences and absence of the position tracking elements disposed in the sequence as the member and corresponding sequence of position tracking elements moves with respect to the probe. Based on the detected presence and absence of position tracking elements, a monitor resource of the position tracking system monitors parameters such as: i) a position of the member along the axis, ii) a rate of movement of the member along the axis over time, iii) a direction of movement of the member along the axis, etc.

16 Claims, 28 Drawing Sheets

Related U.S. Application Data

(60) Provisional application No. 62/683,808, filed on Jun. 12, 2018.

(52) U.S. Cl.
    CPC ... *A61M 5/3157* (2013.01); *A61M 2205/3317* (2013.01); *A61M 2205/3584* (2013.01)

(56) References Cited

U.S. PATENT DOCUMENTS

| | | | |
|---|---|---|---|
| 8,197,449 B2* | 6/2012 | Nielsen | A61M 5/31525 604/207 |
| 10,850,041 B2* | 12/2020 | Larsen | A61M 5/3157 |
| 2004/0111011 A1 | 6/2004 | Uchiyama et al. | |
| 2005/0162804 A1 | 7/2005 | Boronkay et al. | |
| 2009/0062787 A1 | 3/2009 | Schaer et al. | |
| 2011/0270214 A1* | 11/2011 | Jorgensen | A61M 5/31551 604/207 |
| 2011/0313349 A1* | 12/2011 | Krulevitch | G16H 20/17 604/65 |
| 2011/0313395 A1* | 12/2011 | Krulevitch | A61M 5/31525 604/82 |
| 2012/0223724 A1* | 9/2012 | Vasiloiu | G01B 3/004 324/654 |
| 2015/0080762 A1 | 3/2015 | Kassab et al. | |
| 2015/0367079 A1* | 12/2015 | Steel | A61M 5/31525 604/207 |
| 2018/0043105 A1* | 2/2018 | Nazzaro | A61M 5/1452 |
| 2020/0384204 A1* | 12/2020 | Boisdon | A61M 5/31546 |
| 2021/0146062 A1* | 5/2021 | Armiento | A61M 5/20 |

* cited by examiner

ELECTRONIC POSITION SENSING SYSTEM, METHOD, AND APPARATUS

RELATED APPLICATIONS

This application claims priority to PCT application No.: PCT/US2019/036693 filed Jun. 12, 2019 entitled "ELECTRONIC POSITION SENSING SYSTEM, METHOD, AND APPARATUS," which claims priority to U.S. Provisional Patent Application No. 62/683,808 filed Jun. 12, 2018, entitled "DOSAGE DETERMINATION USING ELECTRICAL CIRCUITS IN AN INJECTION DEVICE," the entire teachings of which are incorporated herein by reference.

BACKGROUND

There are a number of conventional medicament delivery devices on the market. They are capable of automatically, semi-automatically, or manually delivering doses of medicament.

Of the known type of delivery devices, the "pen-type" injector is popular and is available in both reusable and disposable designs. Such devices are constructed with dose setting mechanisms that include a variety of inter-acting mechanical components to achieve desired functions, such as setting a dose, dose cancellation, and ultimately delivering the set dose. Such devices are typically designed for non-medically trained individuals to self-administer medicaments.

Users of fluid dispensing devices include diabetics, where medication management and compliance (i.e., the degree to which a patient follows medical instructions and protocols) is often of extreme importance.

To evaluate and determine compliance of a self-medicating user, it is desirable to obtain as much information about each injection as possible, for example, the determination of the actual dose of the medication injected, the amount of the set dose, whether a dose setting correction was needed, the rate of dose injection, whether the injection was halted, the time of day when the injection was performed, and the time required to complete the injection. Collection and evaluation of such data can be especially important if the user is physical impaired, for example, having reduced eyesight or severe arthritis.

BRIEF DESCRIPTION OF EMBODIMENTS

This disclosure includes the observation that, with the need to collect and evaluate the above-identified injection parameters, it would be desirable to provide medication delivery systems that are economical to manufacture and that can monitor and record injection activities or that are ready and capable of working with other devices to monitor, record and report user compliance with injection protocols. As such, embodiments herein include an fluid injection device, preferably a disposable device, that is manufactured in a "ready state" to allow the above-mentioned injection parameters to be measured, recorded, and transmitted so that the collected data can be evaluated by a health care professional. In one embodiment, the "ready state" injection device would be disposable and designed to provide electrical connectors for attachment of a reusable measuring device that can monitor, collect and compute electrical conductivity data from the injection device each time a user performs an injection, thus allowing for cost effective manufacturing of disposable injection devices.

Embodiments herein include a displacement/position tracking system for use various applications such as a fluid dispenser allowing evaluation of user compliance with medical treatment protocols.

More specifically, according to embodiments herein, a displacement/position tracking system includes a member extending along an axis. Multiple position tracking elements (such as conductive strips) are disposed/exposed on the member. The multiple position tracking elements are spaced apart from each other in a sequence along the axis. The position tracking system further includes one or more probe elements that monitor for presence and absence of the position tracking elements disposed in the sequence. Based on detected presence and absence of position tracking elements in the sequence over time, the monitor system is able to track parameters such as: i) a position of the member along the axis, a rate of movement of the member along the axis over time, iii) a direction of movement of the member over time, etc.

In accordance with further embodiments, multiple position tracking elements (such as electrically conductive strips) are disposed in an orthogonal manner with respect to the axis of the member. The spacings between the position tracking elements (electrically conductive strips) is non-electrically conductive material such as plastic, epoxy, ceramic, etc.

In yet further embodiments, the member includes threads disposed thereon. In one embodiment, threads are disposed on an outer surface of the member. The threads spiral on the surface about the member along the axis.

In accordance with still further embodiments, outermost surfaces of the threads are disposed further from an axial center of the member than the sequence of position tracking elements. As further discussed herein, each of one or more sequences of position tracking elements disposed on the member reside on a respective chamfer or ledge formed in the member. This makes it possible to use a control mechanism to apply a force to the threads to move the member, without the control mechanism contacting the position tracking elements.

Note that the probe element in communication with the member and/or sequence of position tracking elements can be based on contact or non-contact sensing. For example, in one embodiment, the probe element as described herein is operative to temporarily contact each of the conductive strips as the member is moved along the axis with respect to the probe element. The detected presence and absence of the position tracking elements along the axis of the member indicates a position of the member with respect to the one or more probe elements monitoring the sequence of position tracking elements. In accordance with further embodiments, the probe element detects when a respective position tracking element is present based on the probe element generating a respective signal in response to the probe element being sufficiently close enough (but not touching) the respective position tracking element.

In accordance with further embodiments, each probe element in the position tracking system (such as an apparatus) includes one or more sensing elements. In one embodiment, each probe element includes a probe element pair such as a first sensing element and a second sensing element. In further embodiments, the position tracking system includes: a sensor circuit in communication with the first sensing element and the second sensing element. The sensor circuit is operable to detect: i) first instances of time in which both the first sensing element and the second sensing element simultaneously contact a respective position tracking element (such as conductive metal strip) in a respective sequence, and ii) second instances of time in which both the first sensing element and the second sensing element do not simultaneously contact a respective position tracking element in the sequence.

Further embodiments of the position tracking system as described herein include a monitor circuit and (software and hardware) processor operable to detect a linear position of the member along the axis with respect to the probe element based on the probe element detecting presence and absence of the conductive strips in the sequence.

In accordance with yet further embodiments, the member includes any number of sequences of conductive strips. For example, the member can be configured to include a first sequence of position tracking elements, a second sequence of position tracking elements, a third sequence of position tracking elements, and so on. In each such sequence, the respective position tracking elements are spaced apart from each other in a manner as previously discussed. In one embodiment, each sequence of the multiple sequences is parallel to the lengthwise axis of the member.

Further embodiments herein include offsetting the position tracking elements in each of multiple sequences with respect to each other on the member. For example, in one embodiment, the position tracking elements in the second sequence are offset along the axis with respect to the position tracking elements in the first sequence. The third sequence of position tracking elements are offset with respect to both the second sequence of position tracking elements and the first sequence of position tracking elements.

Note further that the position tracking system can include any number of probes. In one embodiment, each probe includes one or more probe elements at its tip to detect presence or absence of a respective position tracking element in a sequence. In one embodiment, one probe is configured to monitor presence or absence of a respective sequence of position tracking elements. For example, in one embodiment, a first probe (such as including a corresponding pair of probe elements) is in communication with and monitors a first sequence of position tracking elements; a second probe (such as including a corresponding pair of probe elements) is in communication with and monitors a second sequence of position tracking elements; a third probe (such as including a corresponding pair of probe elements) is in communication with and monitors a third sequence of position tracking elements; and so on. As previously discussed, each of the sequences of position tracking elements can be offset with respect to each other. In one embodiment, detecting movement via the multiple probe sensors provides a better resolution of detecting a position or movement of the member.

In accordance with further embodiments, a single probe element can be configured to include multiple pairs of probe elements that are offset with respect to each other.

Note further that any of the resources as discussed herein can include one or more fabrication resource, monitor resource, computerized devices, controllers, wireless communication devices, gateway resources, mobile communication devices, sensors, servers, base stations, wireless communication equipment, communication management systems, controllers, workstations, user equipment, handheld or laptop computers, or the like to carry out and/or support any or all of the method operations disclosed herein. In other words, one or more computerized devices or processors can be programmed and/or configured to operate as explained herein to carry out the different embodiments as described herein.

Yet other embodiments herein include software programs to perform the steps and operations summarized above and disclosed in detail below. One such embodiment comprises a computer program product including a non-transitory computer-readable storage medium (i.e., any computer readable hardware storage medium) on which software instructions are encoded for subsequent execution. The instructions, when executed in a computerized device (hardware) having a processor, program and/or cause the processor (hardware) to perform the operations disclosed herein. Such arrangements are typically provided as software, code, instructions, and/or other data (e.g., data structures) arranged or encoded on a non-transitory computer readable storage medium such as an optical medium (e.g., CD-ROM), floppy disk, hard disk, memory stick, memory device, etc., or other a medium such as firmware in one or more ROM, RAM, PROM, etc., or as an Application Specific Integrated Circuit (ASIC), etc. The software or firmware or other such configurations can be installed onto a computerized device to cause the computerized device to perform the techniques explained herein.

Accordingly, embodiments herein are directed to a method, system, computer program product, etc., that supports operations as discussed herein.

One embodiment includes a computer readable storage medium and/or system having instructions stored thereon to support fabrication of a position tracking system according to embodiments herein. The instructions, when executed by the computer processor hardware, cause the computer processor hardware (such as one or more co-located or disparately processor devices or hardware) to: receive a member, the member extending along an axis; fabricate multiple position tracking elements on the member, the multiple position tracking elements equally spaced apart from each other in a sequence along the axis; and dispose a probe element to be in communication with the member, the probe element operative to detect a position setting of the member via sensing presence and absence of the conductive strips in the sequence over time.

Another embodiment includes a computer readable storage medium and/or system having instructions stored thereon to support position tracking according to embodiments herein. The instructions, when executed by the computer processor hardware, cause the computer processor hardware (such as one or more co-located or disparately processor devices or hardware) to: receive input from a probe, the probe monitoring a sequence of position tracking elements disposed lengthwise along a member that moves with respect to the probe; identify occurrences of the probe detecting presence and absence of the position tracking elements in the sequence over time based on the input from the probe; and via the detected presence and absence of position tracking elements, produce a position value indicative of a position of the member with respect to the probe.

The ordering of the steps above has been added for clarity sake. Note that any of the processing steps as discussed herein can be performed in any suitable order.

Other embodiments of the present disclosure include software programs and/or respective hardware to perform any of the method embodiment steps and operations summarized above and disclosed in detail below.

It is to be understood that the system, method, apparatus, instructions on computer readable storage media, etc., as discussed herein also can be embodied strictly as a software program, firmware, as a hybrid of software, hardware and/or firmware, or as hardware alone such as within a processor (hardware or software), or within an operating system or a within a software application.

As discussed herein, techniques herein are well suited for use in position sensing such as those used in fluid dispensing from a handheld pen. However, it should be noted that embodiments herein are not limited to use in such applications and that the techniques discussed herein are well suited for other applications as well.

Additionally, note that although each of the different features, techniques, configurations, etc., herein may be discussed in different places of this disclosure, it is intended, where suitable, that each of the concepts can optionally be executed independently of each other or in combination with each other. Accordingly, the one or more present inventions as described herein can be embodied and viewed in many different ways.

Also, note that this preliminary discussion of embodiments herein (BRIEF DESCRIPTION OF EMBODIMENTS) purposefully does not specify every embodiment and/or incrementally novel aspect of the present disclosure or claimed invention(s). Instead, this brief description only presents general embodiments and corresponding points of novelty over conventional techniques. For additional details and/or possible perspectives (permutations) of the invention (s), the reader is directed to the Detailed Description section (which is a summary of embodiments) and corresponding figures of the present disclosure as further discussed below.

Figure 1:
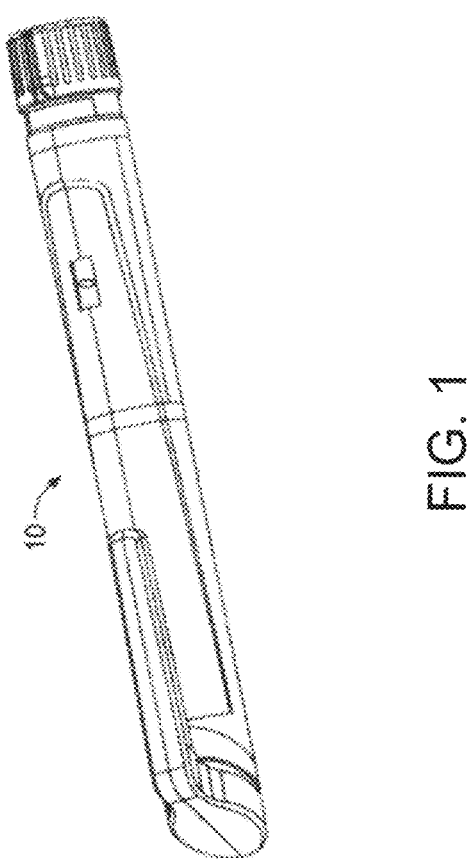
FIG. 1 is an example diagram illustrating a fluid dispensing device according to embodiments herein.

The foregoing and other objects, features, and advantages of the invention will be apparent from the following more particular description of preferred embodiments herein, as illustrated in the accompanying drawings in which like reference characters refer to the same parts throughout the different views. The drawings are not necessarily to scale, with emphasis instead being placed upon illustrating the embodiments, principles, concepts, etc.

DETAILED DESCRIPTION

A position tracking system according to embodiments herein includes a movable member. Multiple position tracking elements (such as conductive strips) are fabricated on a surface of the member in a sequence along a lengthwise axis of the member. The multiple position tracking elements are spaced apart from each other in the sequence. A probe in communication with the member monitors for presence and absence of the position tracking elements disposed in the sequence as the member moves with respect to the probe. Based on detected presence and absence of position tracking elements in the sequence, a monitor resource (such as circuit) of the position tracking system tracks processes the probe information (presence and absence of position tracking elements generated by the probe) and generates tracking information such as: i) a position of the member along the axis over time, ii) a rate of movement of the member along the axis over time, iii) a direction of movement of the member along the axis, etc.

In the present application, note that the term "distal part/end" refers to the part/end of the device, or the parts/ends of the components or members thereof, which in accordance with the use of the device, is located the furthest away from a delivery/injection site of a patient. Correspondingly, the term "proximal part/end" refers to the part/end of the device, or the parts/ends of the members thereof, which in accordance with the use of the device is located closest to the delivery/injection site of the patient.

Now, more specifically, FIG. 1 is an example diagram illustrating a fluid dispensing device according to embodiments herein. One example of fluid dispensing device 10 is a pen-type injector device, which is described below in more detail.

Figure 2:
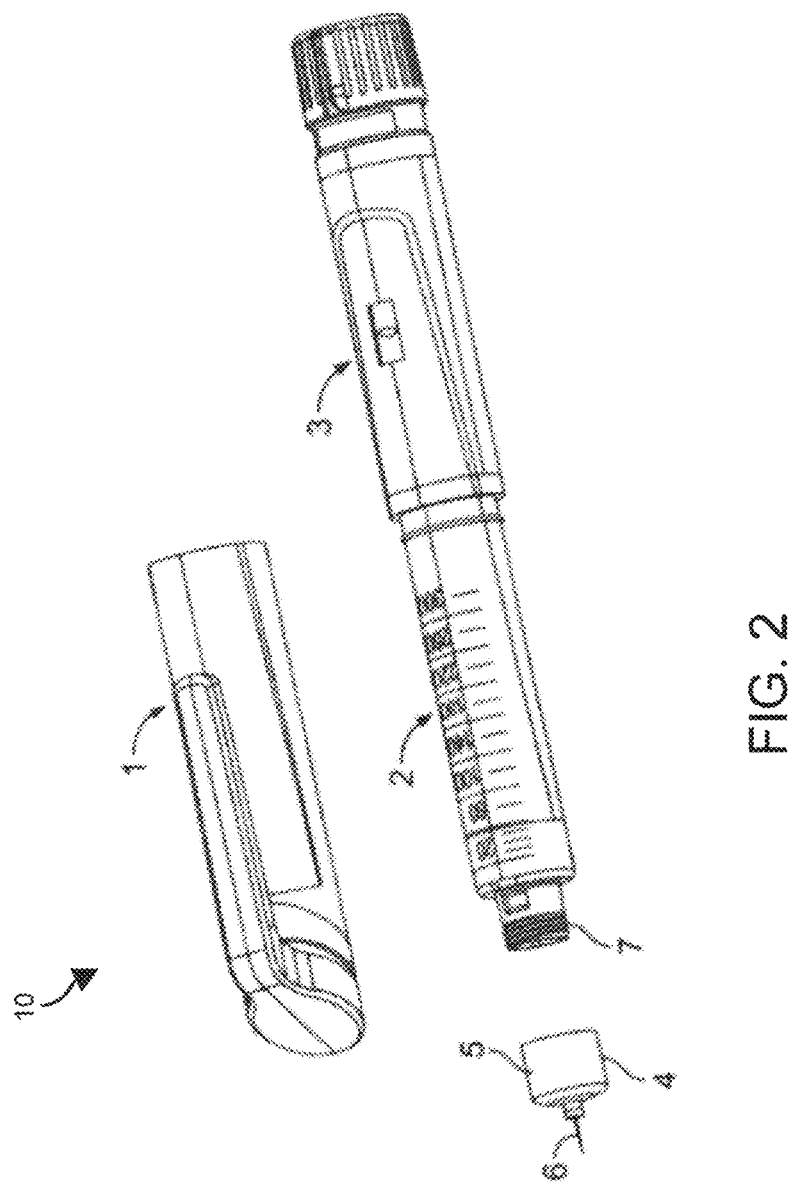
FIG. 2 is an example diagram illustrating a fluid dispensing device according to embodiments herein.

FIG. 2 is an example diagram illustrating a fluid dispensing device according to embodiments herein.

In this example embodiment, cap 1 is removed to expose replaceable needle assembly 4. Needle assembly 4 includes hub 5, canula 6 (dispensing needle). Needle assembly 4 is removable from (threaded) needle connector 7 (distal end of device 10).

Fluid dispensing device 10 further includes cartridge holder 2 and corresponding housing 3.

Figure 3:
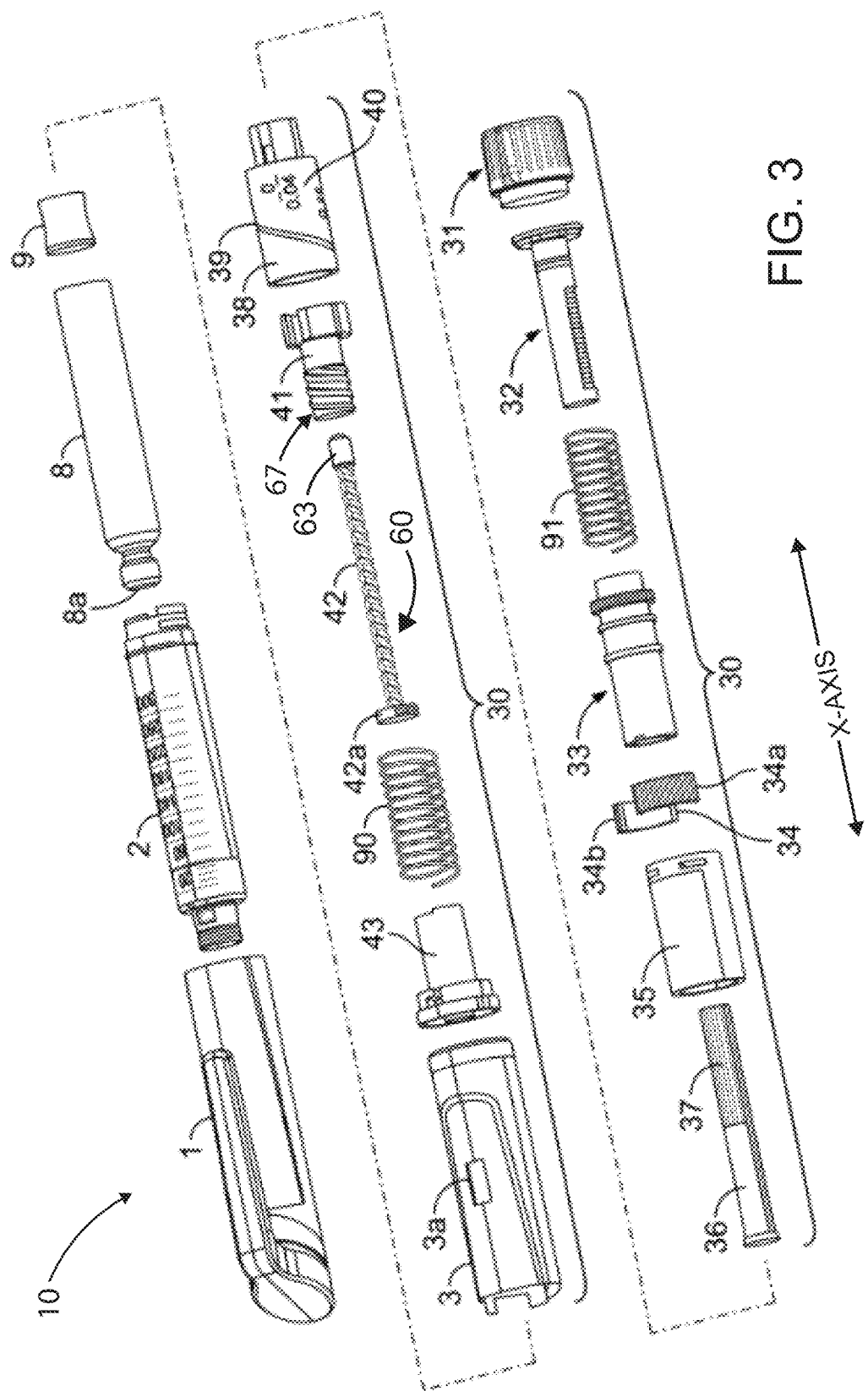
FIG. 3 is an example exploded view diagram of a fluid dispensing device according to embodiments herein.

Further details of the fluid dispensing device 10 are discussed in FIG. 3.

FIG. 3 is an example exploded view diagram of a fluid dispensing device according to embodiments herein.

In this example embodiment, the fluid dispensing device 10 includes a dose setting mechanism 30. The complete fluid dispensing device 10 is illustrated as well as an exploded view of the device, which is presented in the zero dose state as indicated by indicia 40 showing a zero through the window 3a of housing 3.

The fluid dispensing device 10 with cap 1 removed exposes the cartridge holder 2 and the proximal needle connector 7, which is configured for a pen needle 4 (or needle assembly 36) that is typically attached to the needle connector 7 through a snap fit, thread, Luer-Lok, or other secure attachment with hub 5 such that a double ended needle cannula 6 (fluid injection needle) can achieve a fluid communication with medicament (fluid) contained in cartridge 8 positioned within cartridge holder 2.

In one embodiment, the cartridge 8 is sealed at the proximal end by septum 8a and with a sliding piston 9 (or piston disc, bung, stopper) at the opposite distal end.

Although the present disclosure is applicable with a number of injection device designs, the fluid dispensing device 10 illustrated in FIG. 3 is representative of a pen-type injection that has a sleeve 35.

Sleeve 35 translates in a longitudinal direction (along axis X) during dose setting, dose correction, and dose (fluid) dispensing. A dose (amount of fluid to be dispensed) is set through rotation of dose knob 31 (proximal end of device 10), which causes sleeve 35 to move linearly in the distal direction.

In one embodiment, a dose is delivered via the fluid dispensing device 10 by pushing on the end of the dose knob 31 in the opposite or proximal direction. This in turn causes sleeve 35 to move linearly back into the dose setting mechanism in the proximal direction.

The linear movement of the dose selector 35 is a result the outer surface that has one or more longitudinal grooves that are always engaged with longitudinal splines located on the inner surface of housing 3. This engagement prevents relative rotation between the dose selector and the housing, but allows the dose selector to move axially relative to the housing.

In one embodiment, the outer surface of the dose selector 35 also has connecting cut-outs that permanently engage and lock with snap fits on the dose knob 31 such that the dose knob is axially fixed to the dose selector 35. These permanent snap fits allow the dose knob to rotate relative to the dose selector during both dose setting and dose cancellation.

In one embodiment, the particular design of fluid dispensing device 10 allows for setting of one or more of the predetermined fixed doses through the interaction of snap element 33 with dose selector 35. For example, the rotation of the dose knob 31 and snap element occurs during dose setting and is relative to housing 3. During the initiation of the dose delivery procedure, the dose knob 31 is pressed in the proximal direction causing it and the dose selector to move axially relative to the snap element. This initial movement disengages a splined connection and causes engagement of a different spline connection which prevents the doe knob from rotating relative to the housing 3 during dose delivery. The initial movement of the dose selector proximally does not cause movement of the piston rod 42.

Figure 4:
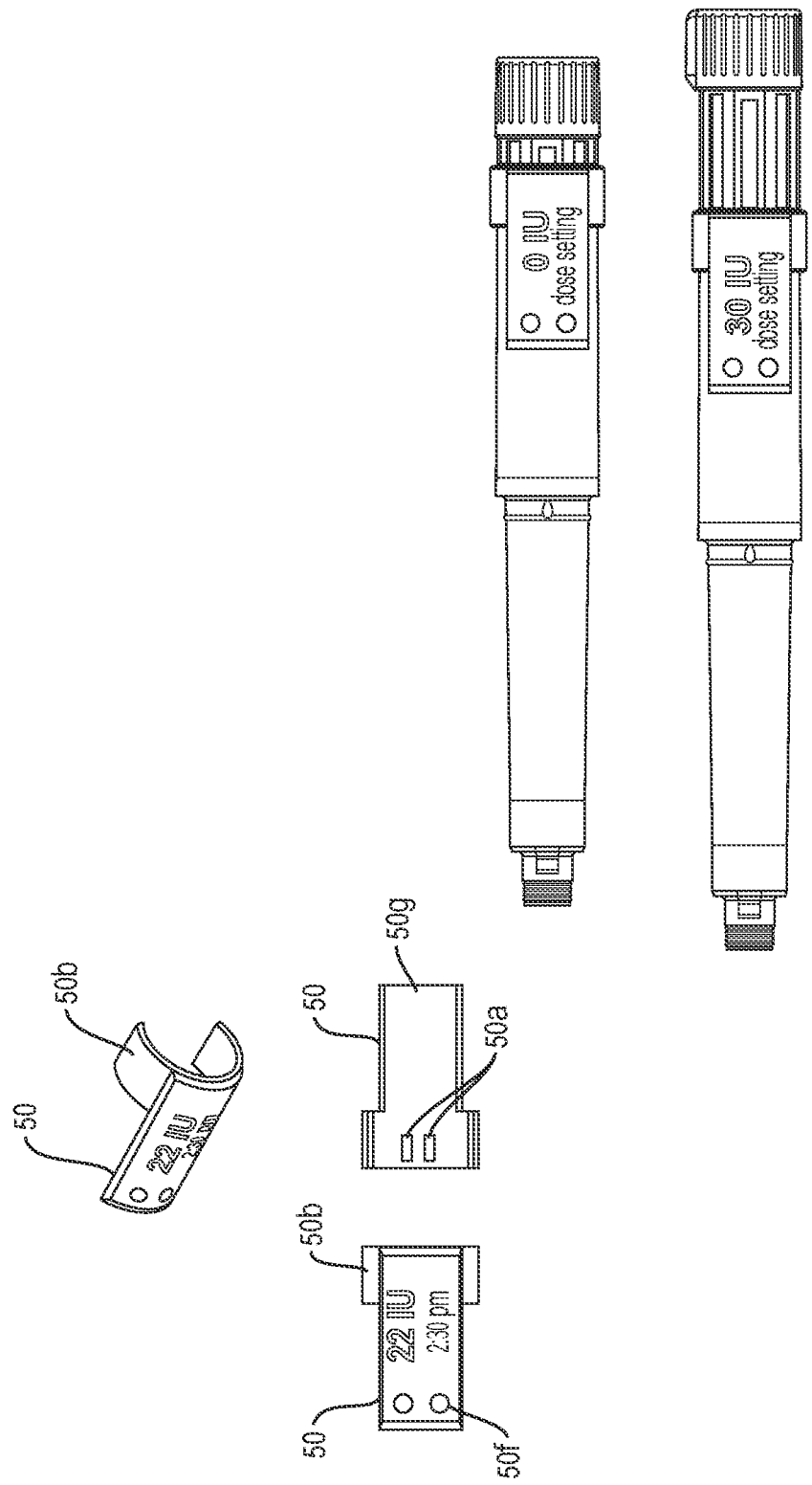
FIG. 4 is an example diagram illustrating elements of a fluid dispensing device according to embodiments herein.

FIG. 4 is an example diagram illustrating elements of a fluid dispensing device according to embodiments herein.

Although the wiper(s) (such as probe or other contact element) and conductive strip(s) or stripes are preferably fixedly attached to the components of the injection device, there can be conductors accessible through the outer housing 3 that are electrically accessible from the outside surface of housing. This allows for connection to an attachable and reusable measuring device 50 (see subsequent figures for an example of such a measuring device) through electrical contacts 50a on the inside surface of measuring device 50. This measuring device could be releasably attached to the injection device outer surface of housing 3 through clips 50b such that electrical connectors 50a on the inside surface 50g will form an electrical connection with connectors on the outside housing of the device. A display 50c is available to present relevant information to the user, such as, for example, the time when the last injection took place 50d, and the dose amount of that last injection 50e. Clearly, other pertinent information could be displayed by the measuring device, such as battery charge level, temperature, alarm status, medicament identification information, connectivity status, etc. the measuring device could also have one or more input features 50f, such as buttons or touch screen features, for the user to press to activate the various features of the measuring device. As explained above the measuring device can measure electrical conductivity in the circuit defined by conductive tracks, strips, stripes, and wiper(s).

Figure 5:
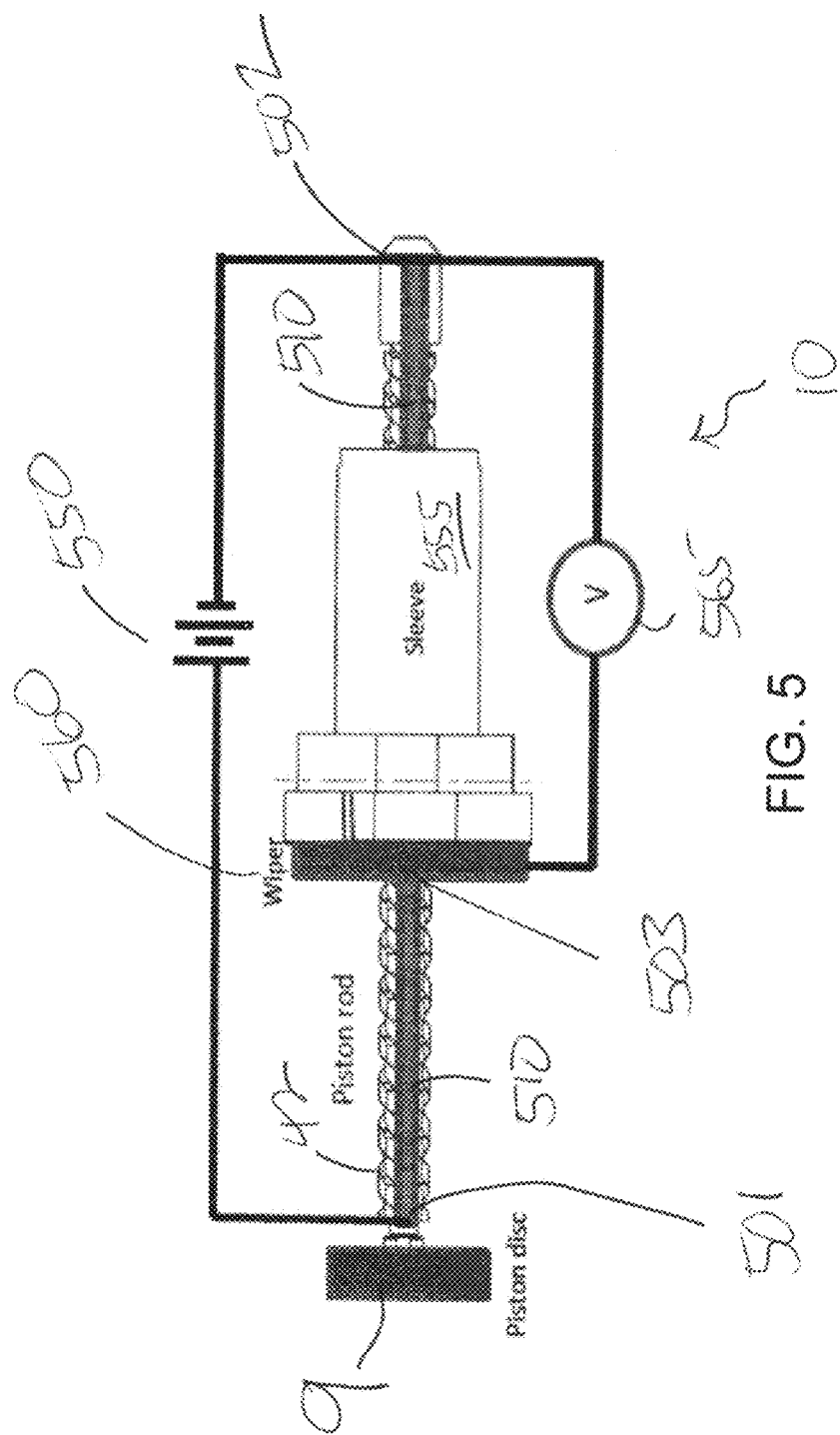
FIG. 5 is an example diagram illustrating a position sensing system incorporated in a fluid dispensing device according to embodiments herein.

FIG. 5 is an example diagram illustrating a position sensing system according to embodiments herein.

In this example embodiment, the piston rod 42 includes a continuous resistive track 510 extending between node 501 and node 502 of rod 42. During operation, battery 550 applies a first reference voltage at node 501 and second reference voltage at node 502. Wiper 560 is in electrical contact (touches) with the location 503 on the track 510. Voltage monitor resource 565 measures a voltage between the location 503 on track 510 and node 502.

Assume that the distance between node 501 and node 502 is 100 centimeters. Further assume that the voltage at node 501 applied by battery 550 is 10 volts and the voltage at node 502 is zero volts. Assume that the monitor resource 565 measures voltage at location 503 as being 6.3 volts. In such an instance, the monitor resource 565 calculates the position of the wiper 560 (or location 503) to be 63 centimeters from node 502. Assume that the monitor resource 565 measures voltage at location 503 as being 3.1 volts. In such an instance, the monitor resource 565 calculates the position of the wiper 560 (or location 503) to be 31 centimeters from node 502.

In this manner, the monitor resource 125 as described herein is able to determine a position of the rod 42 with respect to the sleeve 555.

In accordance with further embodiments, part of the dose setting mechanism of the fluid dispensing device 10 is a piston rod 42. In those device designs, where the piston rod 42 does not rotate during dose delivery, one or more electrically conductive tracks may be applied to or incorporated within the outer or exposed surface of the piston rod as described herein. As further discussed herein, such piston rods can be configured to have a non-circular cross-section and have one or more flat surfaces that are designed to prevent the piston rod from rotating, but allowing it to move linearly in the proximal direction.

Note that one embodiment herein includes measuring the translation of the piston rod such as via applying or otherwise adding a resistive plastic in a pattern along the length of the existing piston rod design by printing or injection molding. This pattern or resistive trace (resistive track 510) is used to form an integrated electrical potentiometer. A voltage can then be applied across the length of the resistive plastic trace. The existing pen is also modified by incorporating an electrical wiper that provides a sliding contact to the resistive plastic on the piston rod. The wiper 560 in contact with the resistive track 510 measures the voltage drop as a function of position along the piston rod as it translates during the drug injection process. The change in voltage can be correlated to the amount of translation of the piston rod which, in turn, can be used to determine the volume of fluid dispensed (i.e. the delivered the dose).

Using existing piston rod designs, the conductive tracks can be applied to or made integral with the flat sides, for example by co-molding. The conductive track (510) can be electrically connected to a wiper 560 (contact probe) that can be incorporated in a piston guide 43 that is linearly fixed to the housing such that the wiper is in sliding electrical contact with the conductive track 510 as illustrated in FIG. 5. In one embodiment, the resistance along the track 510 is uniform such that a voltage along the track linearly varies along the length of the track between the node 501 and node 502.

As the piston rod 42 and piston 9 moves proximally during dose delivery, the length of the conductive tracks decreases, which causes a decrease in the resistance of the circuit defined by the track and the wiper. As previously discussed, monitor resource 565 is electrically connected to the wiper 560 and conductive track 510 to measure a respective resistance (or voltage) indicating position.

In one embodiment, application of the conductive material (associated with track 510) to the piston rod 42 is achieved using a printer capable of printing conductive filaments. In certain instances, conductive filaments are difficult to use in conventional 3D printers because they are also thermally conductive. The heat from the nozzle can conduct up the filament causing softening that can clog the mechanism in the extruder that advances the filament through the nozzle. Extruders with thermal isolation between the nozzle and the gears are required. A custom 3D printer was designed to print conductive filaments on existing piston rods. In one embodiment, the printer is a dual extruder system that enables conductive filaments to be printed along with nonconductive filaments.

The custom printer design requires precise calibration of the extruders and the motion system to enable dual printing without cross contamination of the printed materials. The custom system was used to print structures for material characterization as well as used to print coplanar waveguides. The conductive filament used in this work was a so-called graphene doped PLA manufactured by Black Magic 3D™ of Calverton, NY.

Referring again to FIG. 3 and the dose setting mechanism 30 of device 10, a nut 36 and a clutch 32 are permanently splined to each other during assembly of the dose setting mechanism through a splined connection. The splined connection ensures that clutch 32 and nut 36 are always rotationally fixed to each other during both dose setting and dose delivery. This splined connection also allows the clutch and the nut to move axially relative to each other. The sliding connection allows one to compensate for the difference in the pitch of the thread between nut and the outer surface of the piston rod and the pitch of the thread between dose sleeve and body. The thread between driver and piston guide has basically the same pitch as the thread between piston rod and nut.

The proximal end of nut 36 has internal threads 70 that match threads 60 of piston rod 42. The distal end of clutch 32 is configured as a dose button 72 and is permanently attached to distal end of the dose knob 31 through engagement of connectors, which may also include snap locks, an adhesive and/or a sonic weld. This connection ensures that the clutch is both rotationally and axially fixed to the dose knob during both dose setting and dose delivery.

In addition to threads 60 on the outer surface of the piston rod 42 and the above mentioned two longitudinal flats, the terminal proximal end has a connector 62, shown as a snap fit, that connects with a disc or foot 42*a*. At the distal end of piston rod 42 is a last dose feature of the dose setting mechanism, illustrated as an enlarged section 63. This enlarge section 63 is designed to stop the rotation of nut 36 about threads 60 when the amount of medicament remaining in the cartridge 8 is less than the next highest predetermined dose setting. In other words, if the user tries to set one of the predetermined fixed dose settings that exceeds the amount of medicament remaining in the cartridge, then the enlarged section 63 will act as a hard stop preventing the nut from further rotation along threads 60 as the user attempts to reach the desired predetermined fixed dose setting.

In accordance with further embodiments, the piston rod 42 is held in a non-rotational state relative to housing 3 during both dose setting and dose delivery because it is arranged within the non-circular pass through hole in the center of piston guide 43 (see FIG. 5). The piston guide is both rotationally and axially fixed to housing 3. This fixation can be achieved when the piston guide is a separate component from the housing 3 as illustrated in the figures or the piston guide could be made integral with the housing. Piston guide 43 also engages the proximal end of a rotational biasing member, shown as torsion spring 90, the function of which will be explained below. This connection of the rotational biasing member to the piston guide anchors one end in a rotational fixed position relative to the housing.

The distal end of the rotational biasing member, for example torsion spring 90, is connected to the driver 41. Driver 41 is connected and rotationally fixed with the inner surface of dose sleeve 38 through a splined connection on the distal outer surface of the driver. On the proximal end of driver 41 on the outer surface is threads 67 that are engaged with matching threads on the inner distal surface of the piston guide 43. The thread between driver and piston guide has a significantly different pitch than the thread between dose sleeve and housing. The nut and the driver rotate together both during dose setting and dose cancellation and, as such, they perform essentially the same axial movement. However, this movement is independent from each other, i.e., the nut is turned by the clutch and performs an axial movement due to the thread to the piston rod, while the driver is rotated by the dose sleeve and performs an axial movement due to the thread to the piston guide. The driver is rotating during injection also, and so it actively moves in the proximal direction during injection. In one embodiment, the nut does not rotate during injection and as such does not perform an active axial movement. The nut is only moving in proximal direction during injection because it is being pushed axially by the driver. The rotating driver pushing the non-rotating nut causes the injection because the piston rod is pushed forward due to the threaded engagement with the nut.

If, for example, the thread of the nut had a higher pitch than the thread of the driver, the nut could not freely move in the distal direction during dose setting because it would be hindered by the slower moving driver. As such, this would cause drug to be expelled during dose setting. Alternatively, if the thread of the nut had a significantly lower pitch than the thread of the driver, the driver would move away from the nut during dose setting and the driver would not push the nut at the beginning of the injection already, but would do so only after the gap is closed. Accordingly, it is preferred that the pitch of the thread on the driver is equal or a slightly higher than the pitch of the thread on the nut. And, the thread between the dose sleeve and the housing has a higher pitch than that of the nut and piston rod. This is desirable because it yields a mechanical advantage that makes the dose delivery process easier for the user. For example, when pushing the knob a distance of 15 mm (millimeter), the piston rod only moves by 4.1 mm. This results in a gearing ratio of about 3.6:1. A lower gearing ratio would result increase the force the user needs to complete the injection.

Because the torsion spring is attached to the driver 41 and the driver is rotationally fixed to the dose sleeve 38, then rotation of the dose sleeve in a first direction during dose setting will wind the torsion spring such that it exerts a counter rotational force on the dose sleeve in an opposite second direction. This counter rotational force biases the dose sleeve to rotate in a dose canceling direction.

In another embodiment of the present disclosure that enables electronic measurement of the dispensed dose from a pen-type drug injection device based on accurately measuring the translation of the piston rod involves the use of closely-spaced, parallel, conductive lines that are fabricated onto the flat surface of the piston rod by a printing or injection molding process. These parallel conductive lines are preferably printed onto the piston rod using the custom printer described above. The conductive lines are oriented perpendicular to the direction of the piston translation during dose delivery. The metal stripes can be printed using a silver nano-ink on a Nordson™ dispensing system.

In accordance with further embodiments, a stationary electrical wiper (i.e., probe), comprising two metal probes (probe elements) with a voltage applied across them, is also incorporated into the pen design. As the piston rod translates during the injection process under the wiper, the two metal probes on the wiper come into contact with the conductive lines on the piston rod. When the two wiper probe elements make contact with a conductive trace on the piston rod a closed circuit is created and current flows in the wiper circuit. As the piston rod translates axially relative to and under the wiper arm, the wiper probes move on and off the conductive lines on the piston rod, creating a series of current pulses detected and tracked by a digital counter. The number of current pulses detected during the piston rod translation (i.e., during the injection process) determines the number of conductive traces that have translated under the stationary wiper.

This monitored and recorded number of conductive traces is directly proportional to the amount of medicament expelled from the container and delivered to an injection site. The required measurement accuracy can be designed into the pen by controlling the spacing between the conductive traces fabricated on the piston rod. Preferably, the accuracy should be of the order of about 0.14 mm. This movement of the piston rod equals to an expelled volume of 0.01 ml, when a standard cartridge is used.

The translational movement metal stripes (i.e., position tracking elements) that are printed on the piston rod 42 (such as member 1200 as further discussed herein) perpendicular to translational direction (axis X) are spaced at intervals that can adjusted to achieve the desired dosage resolution. In other words, the conductive strips (such as made of metal or other electrically conductive material or position tracking elements 650 are disposed lengthwise along axis Y. As mentioned, the translation of the stripes is detected by measuring electrical continuity between probe elements on the wiper (probe) as the metal stripes translate during dose injection. In one embodiment, the wiper probes move alternately from "on-stripe" to "off-stripe" detection position, essentially defining a digital scheme, making such a design readily acceptable to an interface with processing electronics.

Figure 6:
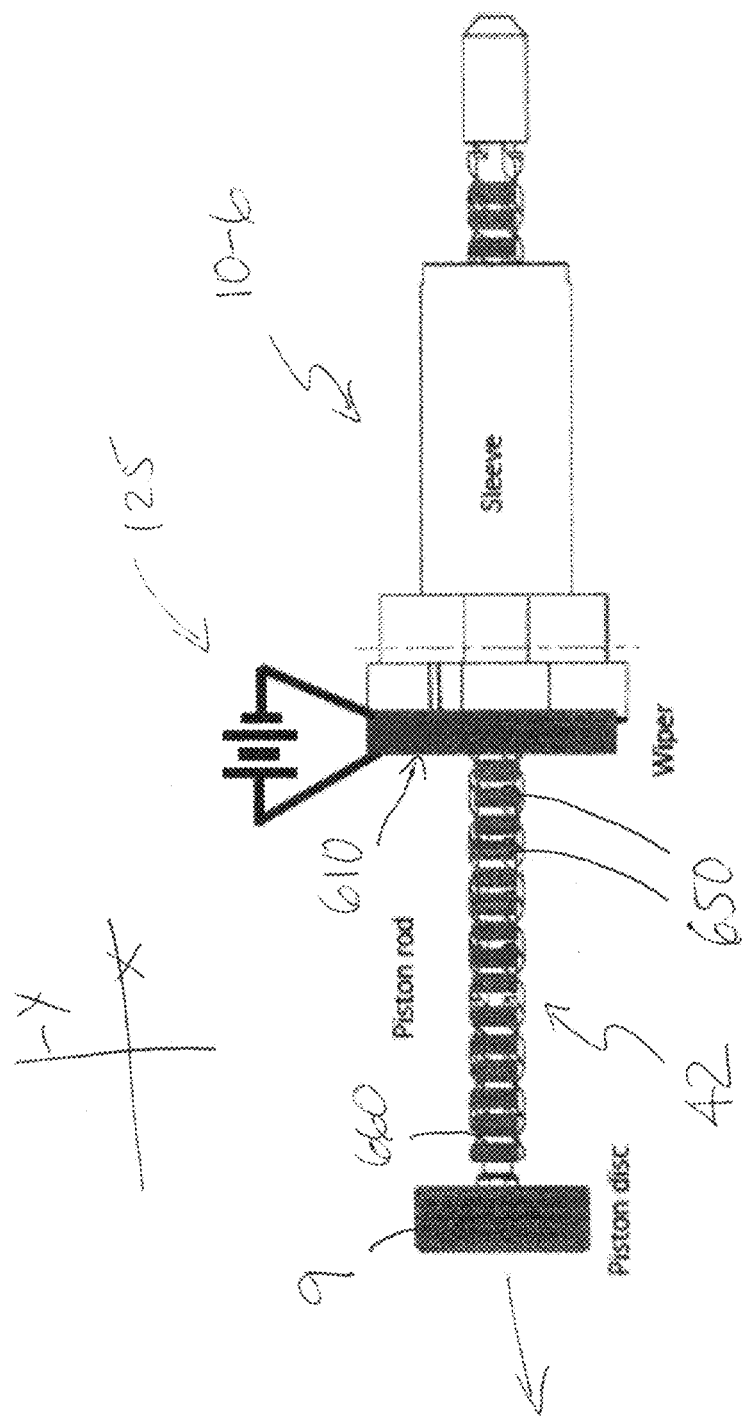
FIG. 6 is an example diagram illustrating a position sensing system incorporated in a fluid dispensing device according to embodiments herein.

Note that unlike the analog approach described above (in FIG. 5) where a continuous strip of conductive material (track 510) is applied to or incorporated into the piston rod 42, FIG. 6 implements a parallel series of conductive stripes in rod 42 of the device 10-6 to measure position. Such a design is immune to noise and other external sources of interference.

In this example embodiment, as previously discussed, the rod 42 includes conductive strips 650 spaced apart via spaces 660. In one embodiment, the conductive strips 650 are fabricated from metal or other electrically conductive material. Spaces in between the conductive strips are fabricated from non-electrically conductive material. In one embodiment, each of the conductive strips is spaced apart by an equal distance from a next adjacent conductive strip in a sequence.

Device 10-6 further includes probe 610 that is in contact with the sequence of conductive strips 650 and spaces 660 spaces on rod 42 depending on a position of rod 42. When current flows through two probe elements of the probe 610, the probe detects contact of the probe 611 with a respective conductive strip. Conversely, when no current flows through the two probe elements of the probe 610, the probe detects contact of the probe 611 with a respective spacing 660 between conductive strips. As previously discussed, detecting presence and absence of the conductive strips (position tracking elements) indicates an amount of translation of the rod 42 (or member 1200) along the x-axis.

In one embodiment, the fluid volume dispensed by the injection pen is determined by the linear translation of a threaded piston rod 42 that in turn pushes a slidable piston 9 (bung or stopper) within the drug cartridge 8. In a number of pen-type injection devices, the user is able to manually adjust the desired dose setting by manipulation (e.g., turning a dose setting knob) of a mechanical component of the injection pen. In the case, where the pen design has a dose setting knob 38, the knob (or a button associated with the knob) is then pushed to translate the piston rod axially in a distal direction within the pen to displace the drug from the cartridge. Measurement of the piston rod 42 translation is correlated to calculate the volume of fluid dispensed. The conductive lines (conductive strips 650) added to an existing piston rod design can comprise a silver nano-ink that is printed directly on the piston rod. The wiper (probe 610) can be composed of any suitable material such as a conductive elastomer. For example, the wiper can be made from a piece of flexible Kapton which had the two conductive traces/probes printed on it. A very small battery can be incorporated into device 10 and monitor circuit 125 to supply the needed voltage potential to detect the conductive strips.

As previously discussed, as the piston rod 42 translates (to the left) during the injection process under the wiper probe 610, the two conductive probe elements on the wiper probe 610 come into contact with the conductive lines (conductive strips or position tracking elements) on the piston rod 42. When the two wiper probes make contact with a conductive trace on the piston rod a closed circuit is completed and current flows in the wiper circuit.

As the piston rod translates under the wiper arm, the wiper arm traces (probe elements) move on and off the conductive lines (position tracking elements) on the piston rod 42, creating a series of current pulses that can be detected by a digital counter (such as monitor circuit 125).

The number of current pulses detected during the piston rod translation (i.e., during the injection process) determines the number of conductive traces that have moved under the stationary wiper arm (probe 610) and thus the total translation of the rod during injection. The minimum translational measurement accuracy is determined by the pitch (d) between the conductive traces on the piston rod 42. One possible design of such a piston rod is shown in FIGS. 7A and 7B, which has been patterned with conductive lines that are oriented perpendicular (such as along or parallel to the Y-axis) to the direction of piston translation.

Figure 7:
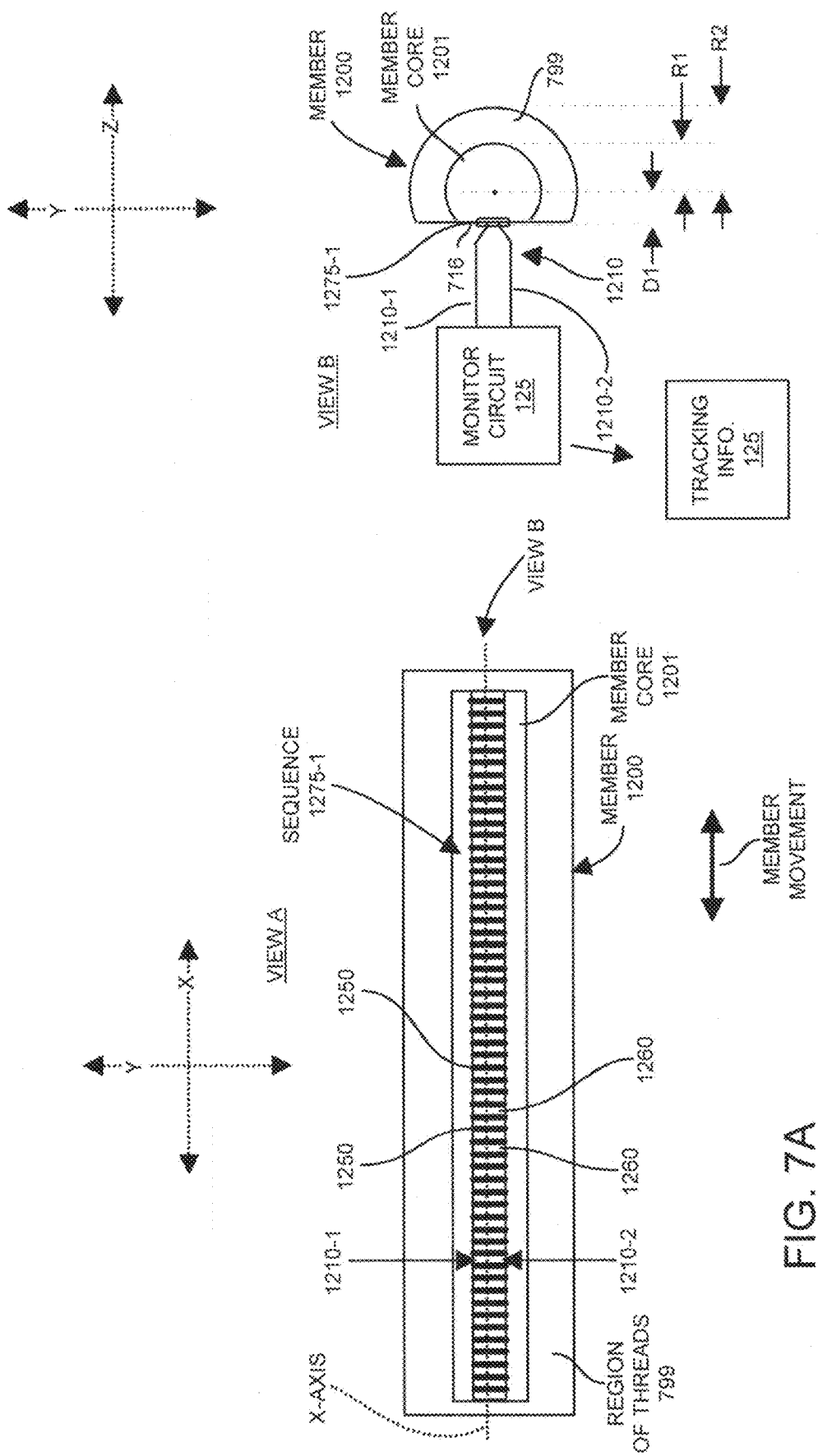
FIG. 7A is an example side view diagram illustrating a sequence of position tracking elements axially disposed on a member according to embodiments herein.
FIG. 7B is an example axial view diagram illustrating a sequence of position tracking elements axially disposed on a member according to embodiments herein.

FIG. 7A is an example side view diagram illustrating a sequence of position tracking elements disposed on a member along an axis according to embodiments herein.

In this example embodiment, the member 1200 (such as rod 42) includes a sequence 1275-1 of position tracking elements 1250 (conductive strips along and parallel to X-axis) spaced apart by spacings 1260. Member 1200 includes region of threads 799 (see FIG. 8 for threads).

Referring again to FIG. 7A, probe 1210 includes probe element 1210-1 and probe element 1210-2.

Probe 1210 is in communication with monitor circuit 125. During a condition in which both the probe element 1210-1 and probe element 1210-2 contact a same position tracking element (conductive strip), the monitor circuit 125 detects a low impedance condition between the probe element 1210-1 and probe element 1210-2. This indicates presence of a respective position tracking element (conductive strip).

Conversely, during a condition in which one or both of the probe element 1210-1 and probe element 1210-2 contact a same spacing (absence of a conductive strip or non-electrically conductive material), the monitor circuit 125 detects a high impedance condition between the probe element 1210-1 and probe element 1210-2. This indicates absence of a respective position tracking element (conductive strip).

FIG. 7B is an example axial view diagram illustrating a sequence of position tracking elements disposed on a member along an axis according to embodiments herein.

In this example embodiment, the sequence 1275-1 of position tracking elements is disposed on a chamfer 716 or ledge or flat portion of inside radius R1 of the member core 1201.

As previously discussed, in FIG. 7B, member 1200 moves in a direction on X-axis, in and out of the drawing. Probe elements 1210-1 and 1210-2 monitor for presence and absence of position tracking elements on sequence 1275-1.

Distance D1 indicates a distance of the sequence 1275-1 with respect to a center of the member core 1201. R1 represents a measure of the radius of the member core 1201 (where there are no threads on member 1200). R2 represents a measure of the radius of the member 1200 including respective threads. In other words, in one embodiment, threads of the member 1200 reside outside of radius R1 and to the inside of radius R2. There are no threads on the ledge or chamfer in which the sequence 1275-1 of position tracking elements reside.

Figure 8:
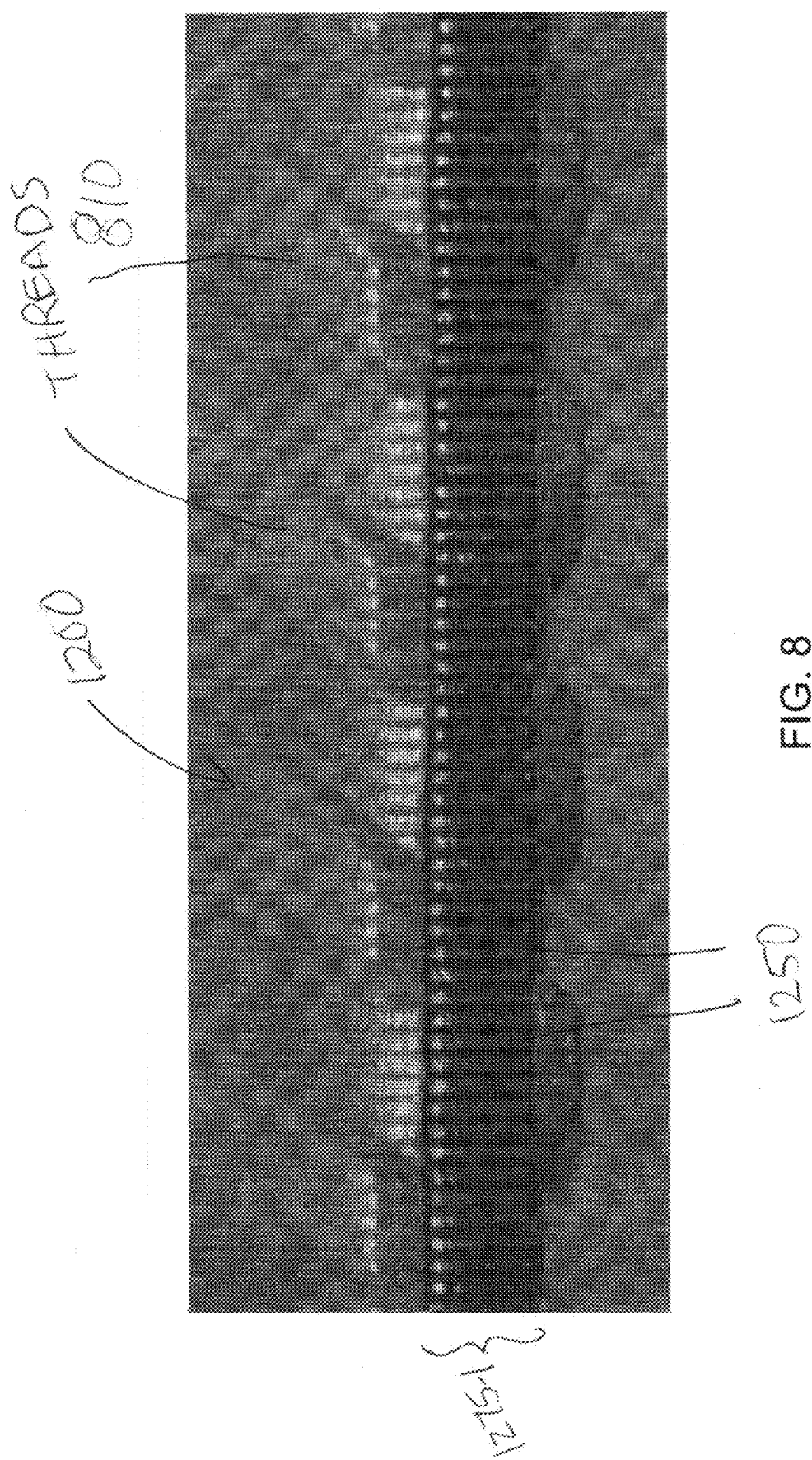
FIG. 8 is an example 3-D view of a sequence of displacement tracking elements disposed on a member according to embodiments herein.

FIG. 8 is an example 3-D view of a sequence of displacement tracking elements disposed on a member according to embodiments herein.

As shown, member 1200 includes threads 810 and sequence 1275-1 of position tracking elements 1250. Presence of threads enables application of a force (via rotation of a mechanical element in contact with the threads) to move the member 1200 (a.k.a., rod 42). The mechanical element has an inner diameter greater than 2 times the radius R1 such that the mechanical element applies a force to the threads 810, but does not interfere or contact the sequence 1275-1 of position tracking elements 1250 residing on chamfer 716.

Referring again to FIG. 3, accordingly, the wiper (probe) can be integrated into the end piston guide 43. The two wiper probes come into contact and out of contact with the conductive traces as the piston rod translates under the wiper. One embodiment of a wiper (probe 610) is shown in FIG. 6, which was made from a piece of flexible Kapton having two conductive traces/probes printed on it.

Note that an advantage of the described embodiments including position tracking elements is that it is purely digital and only requires the detection of electrical continuity to measure the translation of the piston rod. The measurement accuracy is determined primarily by the spacing of the conductive traces on the piston rod. This allows the manufacturer to design the requisite measurement accuracy required for the injection pen by closing the line spacing. Another advantage of this digital approach is that there is no need for analog measurement of an electrical parameter (e.g., resistance or capacitance) that can introduce errors caused by noisy contacts, EMI interference, or structural/material variations.

Figure 9:
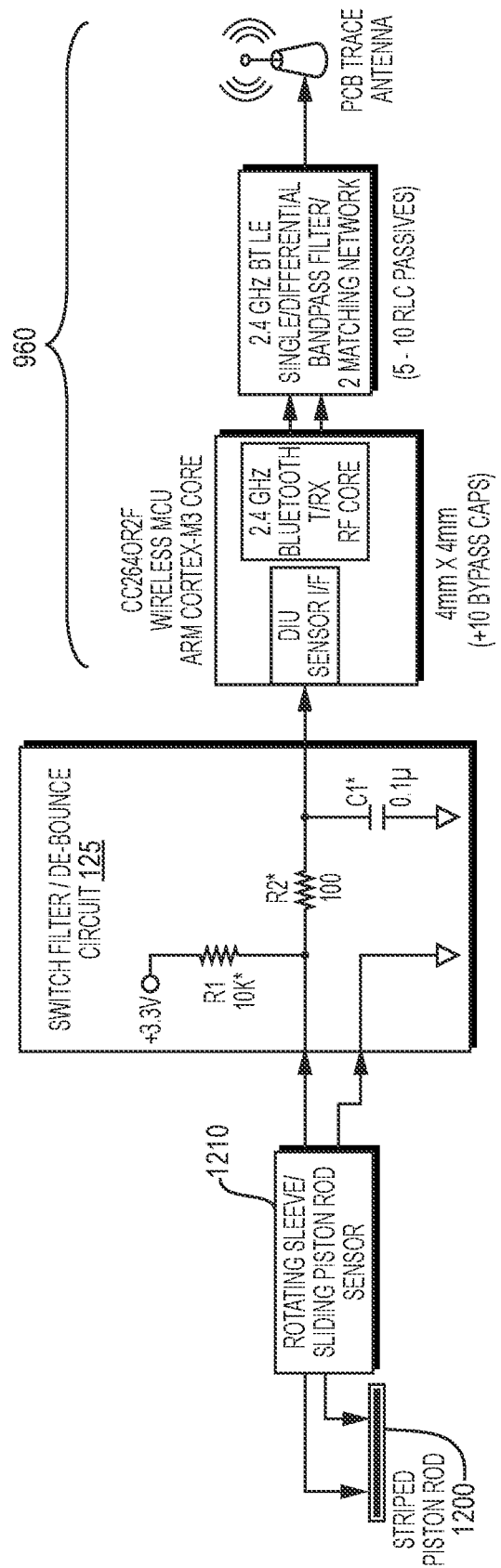
FIG. 9 is an example diagram illustrating implementation of displacement tracking system according to embodiments herein.

The electronics built into the pen must count the number of completed circuits (indicated by the presence of a current pulse) as the wiper comes into contact with each conductive trace on the piston rod. The circuit should also include a means for eliminating contact bounce, which can create false counts. In addition, the electronics should include a means for wireless communication using a low power protocol such as Bluetooth™. The electronics can take many forms. FIG. 9 shows one possible embodiment that also includes the wireless connectivity via a Bluetooth™ protocol.

More specifically, FIG. 9 is an example diagram illustrating displacement tracking system according to embodiments herein.

In a manner as previously discussed, the probe 1210 monitors a position of the member 1200. In this example embodiment, the monitor circuit 125 of device 10-9 includes a debounce circuit to detect presence and absence of the position tracking elements on the sequence 1275-1. The debounce circuit prevents noisy switch transitions form being counted as detected a next position tracking element in a sequence.

As further shown in FIG. 9, in addition to including a member 1200 and a respective monitor circuit 125, the device 10-9 includes a wireless interface 960 coupled to the monitor circuit 125. During operation, wireless interface 960 communicates tracked information 1072 over a wireless communication link to a target device that monitors position information 1072 and/or fluid dispensing.

Figure 10:
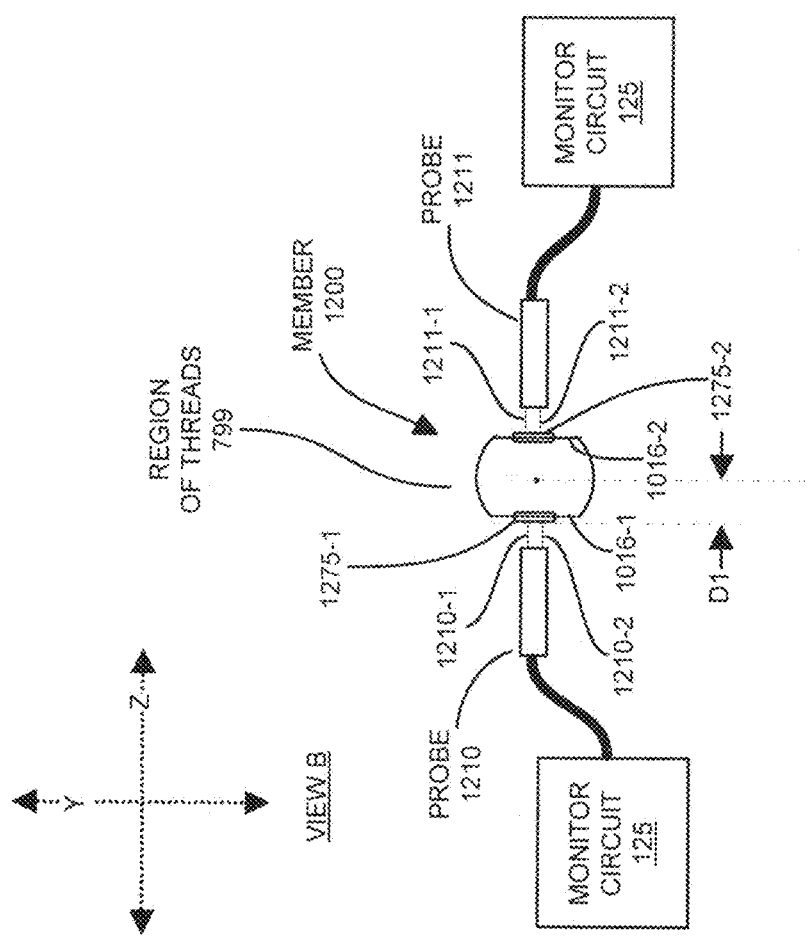
FIG. 10 is an example axial view diagram illustrating a sequence of displacement tracking elements disposed on a member according to embodiments herein.
Figure 11:
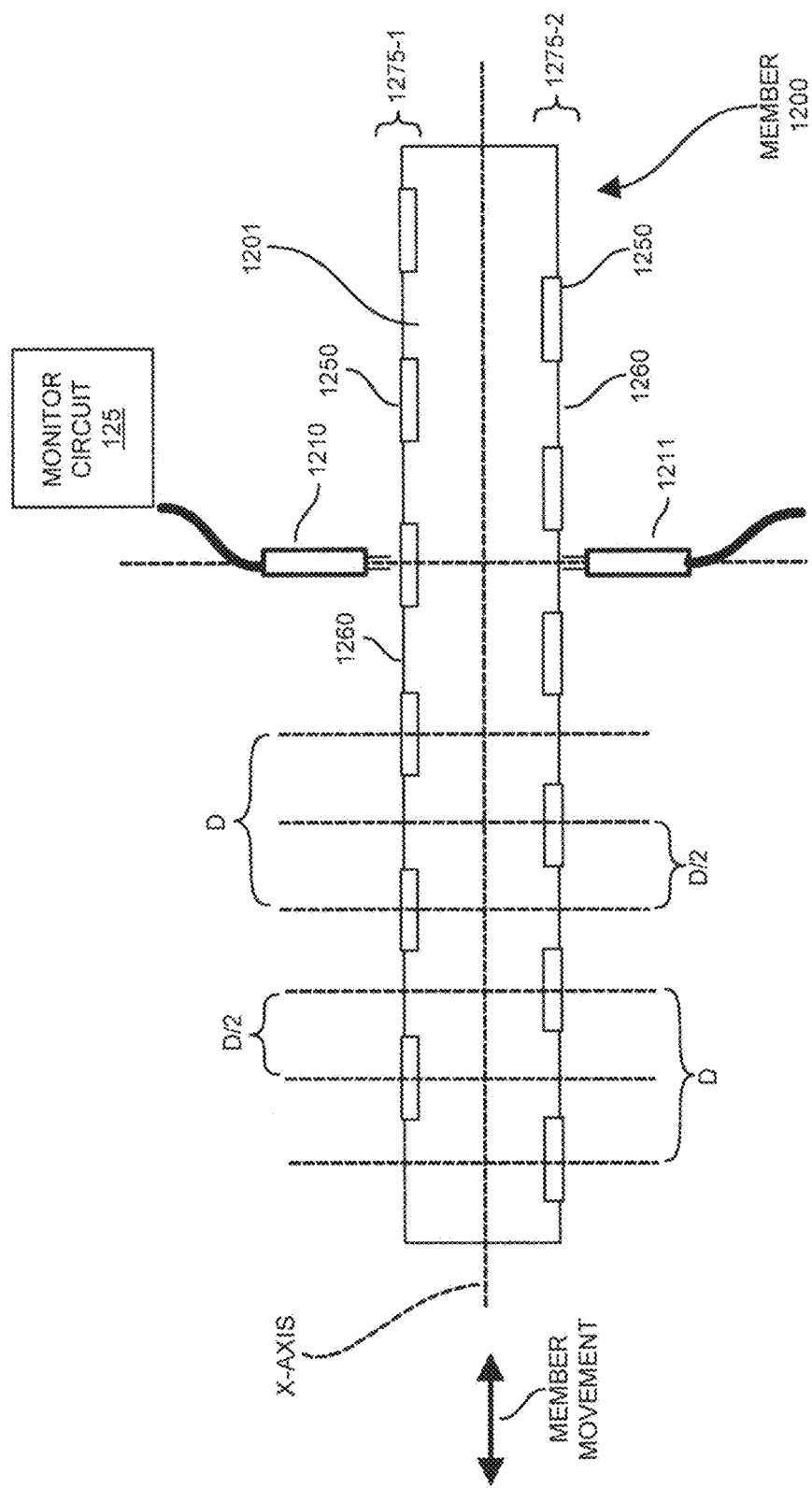
FIG. 11 is an example side view diagram (associated with FIG. 10) illustrating multiple sequences of displacement tracking elements disposed on a member according to embodiments herein.

FIG. 10 is an example axial view diagram illustrating a sequence of displacement tracking elements disposed on a member along an axis according to embodiments herein. Note that a side view of the member 1200 in FIG. 10 is shown in FIG. 11.

Referring again to FIG. 10, the member includes multiple sequences 1275-1 and 1275-2 of position tracking elements. In this example embodiment, monitor circuit 125 includes two probes, namely, probe 1210 and 1211.

Probe 1210 includes probe element 1210-1 and 1210-2.

Probe 1211 includes probe element 1211-1 and 1211-2.

Probe 1210 monitors sequence 1275-1 of position tracking elements on chamfer 1016-1 of member 1200. Probe 1211 monitors sequence 1275-2 of position tracking elements on chamfer 1016-2 of member 1200.

Monitor circuit 125 produces tracking information 1072 in similar manner as previously discussed. Further details of the sequences 1275 of position tracking elements are further discussed in FIG. 11.

FIG. 11 is an example side view diagram illustrating multiple sequences of displacement tracking elements disposed on a member along an axis according to embodiments herein.

In this example embodiment, the probe 1210 and corresponding probe elements monitor for presence and absence of position tracking elements 1250 on sequence 1275-1. The probe 1211 (disposed 180 degrees opposite probe 1210) and corresponding probe elements monitor for presence and absence of position tracking elements 1250 on sequence 1275-2.

Sequence 1275-1 of position tracking elements 1250 is offset by an amount D/2 with respect to sequence 1275-2 of position tracking elements 1250. Each of the position tracking elements is spaced apart by distance, D. As previously discussed, spacings 1260 (non-electrically conductive regions) indicate absence of position tracking elements 1250.

Monitoring of multiple sequences 1275 provides a better position detection resolution.

Thus, in yet two other possible embodiments, the piston rod 42 (or m ember 1200) as described herein can be configured with two sets of conductive lines (sequences 1275) as illustrated in FIG. 11. Such a configuration can be used to relax the required pitch between conductive lines to achieve the required injected dose. This is accomplished by fabricating the piston rod with another set of conductive lines (such as sequence 1275-1 and sequence 1275-2) on the opposite side of the piston rod. The addition of a second wiper will allow the same number of current pulses to be created (during piston translation) with twice the pitch of a piston rod that has only a single side of the piston rod containing the conductive lines.

Note that the position tracking elements in a respective sequence can be flush with a surface of the member, recessed with respect to the surface of the member, or protruding from a surface of the respective member.

Some of the advantages of using the parallel stripe design include no analog measurements required, thereby reducing power requirements and circuit complexity (e.g., no amplifiers). It also reduces PCB size since fewer components are required and eliminates internal and external noise as a possible source of error in dosage measurements, thereby simplifying the interface circuitry.

Additionally, software requirements are simplified since there is no need to run further DSP filter routines, (which also saves on processor power, prolonging battery life). Simple electrical connection of electronics between the wiper arms is also realized. This minimizes the number of electrical connections required (compared with other designs) that should provide lower manufacturing costs and improved product reliability. Required dosage accuracy of 0.01 mL (or 140 microns) can be mechanically guaranteed by the physical pitch of the metallic stripes on the piston rod. No complex software algorithms are needed to ensure accuracy as the software only needs to count the number of stripes it encounters as the piston rod translates.

Resolution and accuracy can also be adjusted to suit the requirements of the pen by tailoring the dimensions of the stripes and wiper arm. Such a design enables the resolution to be adjusted between product lines as needed. Absolute precision in the line width or thickness of the metal stripes is not required since simple electrical continuity is all that is required to sense the presence of a line as the stripes translate with the piston rod under the wiper.

The materials of construction of the piston rod can affect the application of the conductive material to the outer surface of the piston rod. The rough surface of an acetal piston rod makes it difficult to print closely spaced metal lines. Accordingly, the parallel metal lines (stripes) could be printed using a Nordson printer on a smooth piece of Kapton tape, which can then be subsequently attached to the piston rod. The printed metal could be subsequently sintered using a Novacentrix Photonic Curing system.

FIGS. 12-15 are example side view diagrams illustrating measurement of displacement (position) based on sensing of position tracking elements according to embodiments herein.

Figure 12:
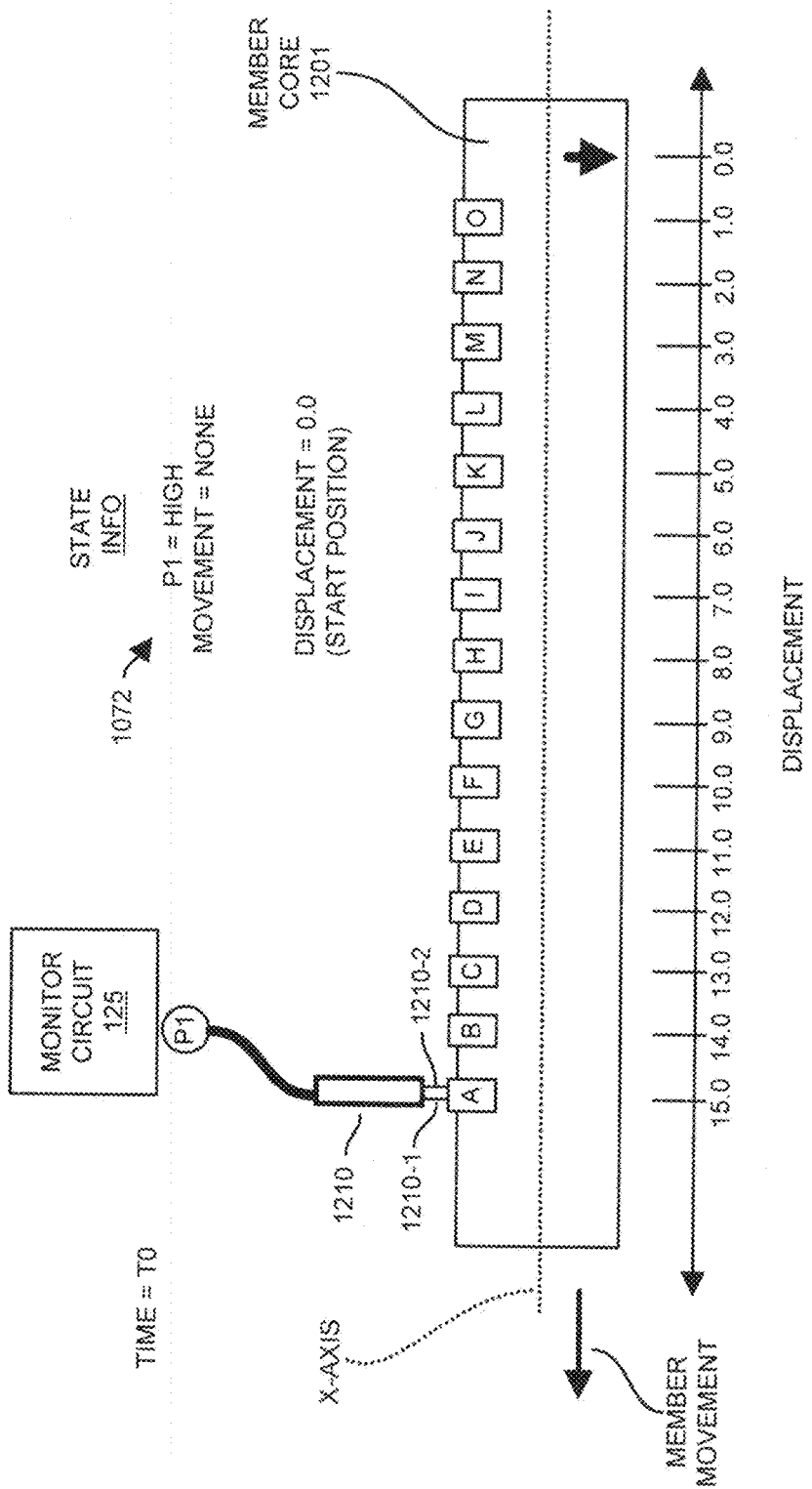
FIGS. 12-15 are example side view diagrams illustrating measurement of displacement (position) based on sensing of position tracking elements according to embodiments herein.

More specifically, FIG. 12 is an example diagram illustrating detection of a position tracking element according to embodiments herein.

Assume in this example embodiment that the member 1200 and core 1201 can move only to the left along axis X.

For example, at its rightmost position (for example, starting position), the member 1200 has a position displacement of 0.0 units. In such an instance, both the probe element 1210-1 in the probe element 1210-2 of the probe 1210 contact the position tracking element a disposed on the member 1200. In such an instance, because of the detected low resistance path provided by the position tracking element A between probe element 1210-1 and 1210-2, the monitor circuit 125 produces the tracking information 1072 (including state information, HIGH indicates detection of a position tracking element) to indicate that the member 1200 is disposed at displacement equal to 0.0 at time T0.

Assume that the member 1200 moves to the left along the X-axis. Detection of the new position of the member 1200 is shown in FIG. 13.

Figure 13:
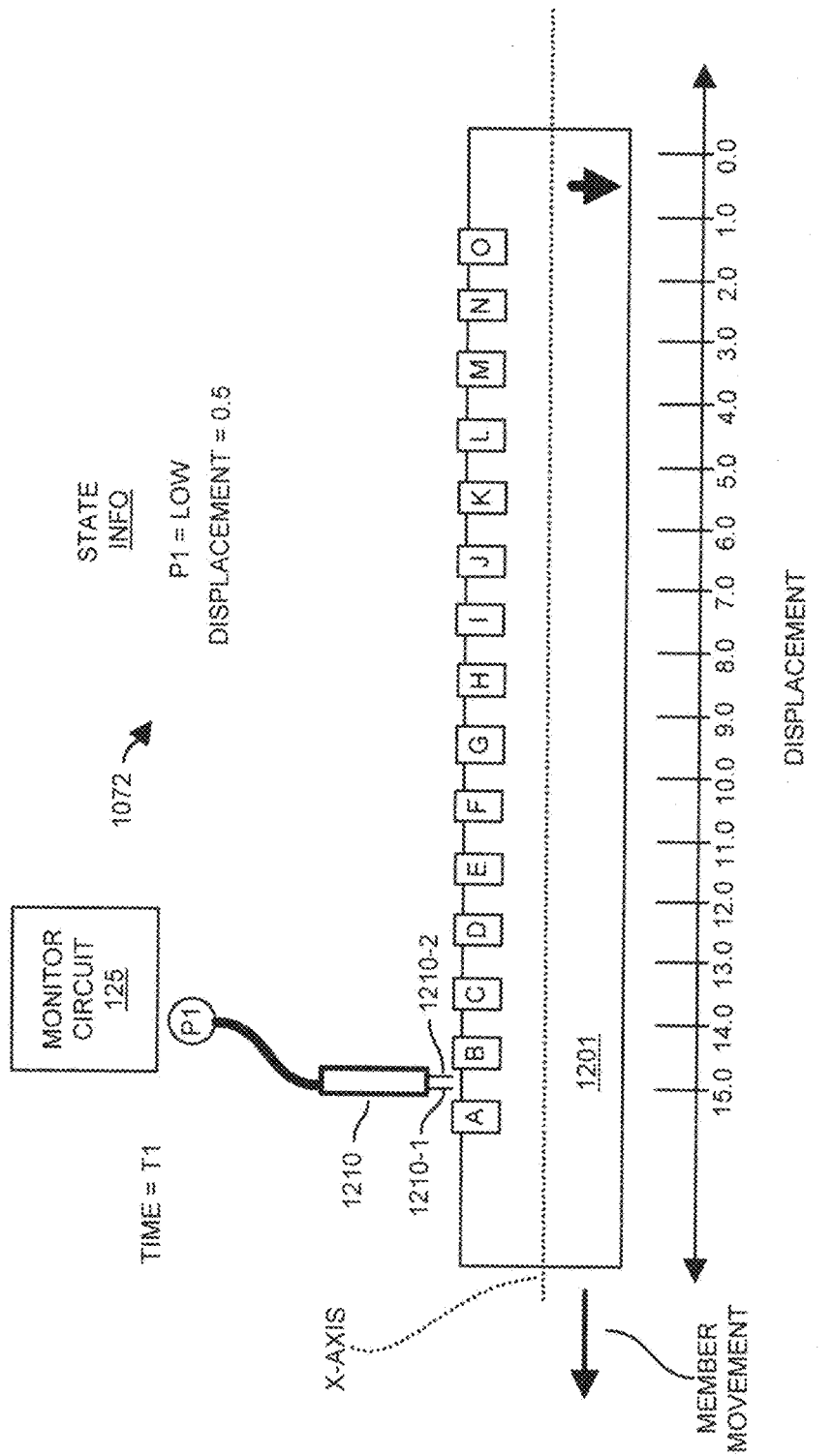

FIG. 13 is an example diagram illustrating detection of a position tracking element according to embodiments herein.

Based on movement of the member 1200 to the left along the x-axis, the member 1200 (or member core 1201) now has a position displacement of 0.5 units at time T1. Recall that core 1201 is made of non-electrically conductive material. In such an instance, both the probe element 1210-1 and the probe element 1210-2 of the probe 1210 are in contact with or are over a respective spacing between the position tracking element A and position tracking element B disposed on the member 1200. In such an instance, because no current flows through a position tracking element and respective probe elements 1210-1 and 1210-2, and because of the detected transition from a low resistance path provided by the position tracking element A to a high resistance path between probe element 1210-1 and 1210-2, the monitor circuit 125 produces the tracking information 1072 (including state information, LOW indicates absence of detection of a position tracking element) to indicate that the member 1200 is now at position equal to 0.5 at time T1.

Assume that the member 1200 moves to the left along the x-axis again. Detection of the new position of the member 1200 is shown in FIG. 14.

Figure 14:
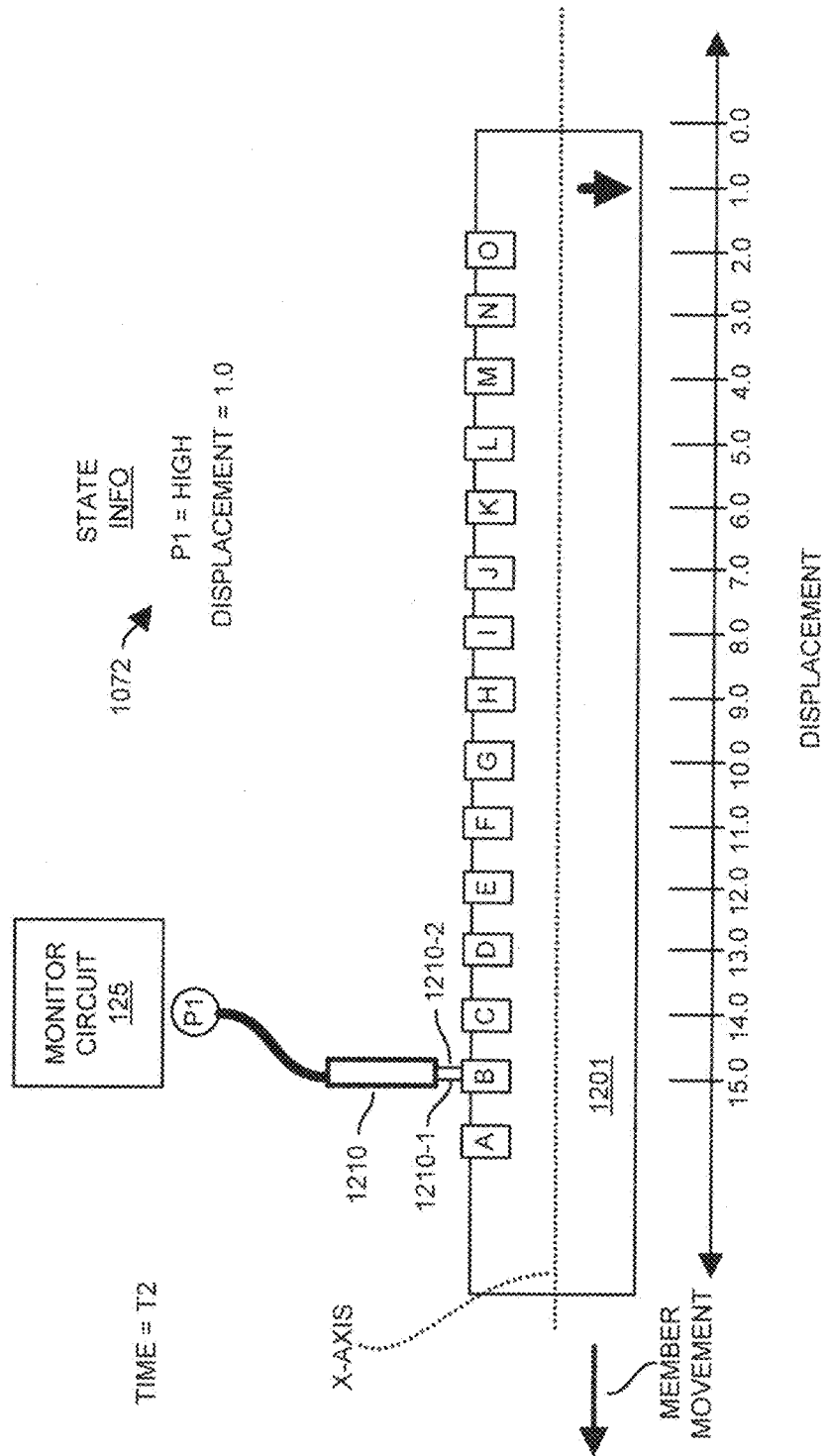

FIG. 14 is an example diagram illustrating detection of a position tracking element according to embodiments herein.

Based on movement of the member 1200 to the left along the x-axis, the member 1200 (and corresponding core 1201) now has a position displacement of 1.05 units at time T2. In such an instance, both the probe element 1210-1 and the probe element 1210-2 of the probe 1210 contact a respective position tracking element B disposed on the member 1200.

In such an instance, because current flows through probe elements 1210-1 and 1210-2 and position tracking element B, and because of the detected transition from a high resistance path to a low resistance path between probe element 1210-1 and 1210-2, the monitor circuit 125 produces the tracking information 1072 (including state information, HIGH indicates detection of a position tracking element) to indicate that the member 1200 is now at position equal to 1.0 at time T2.

Assume that the member 1200 moves to the left along the x-axis again. Detection of the new position of the member 1200 is shown in FIG. 15.

Figure 15:
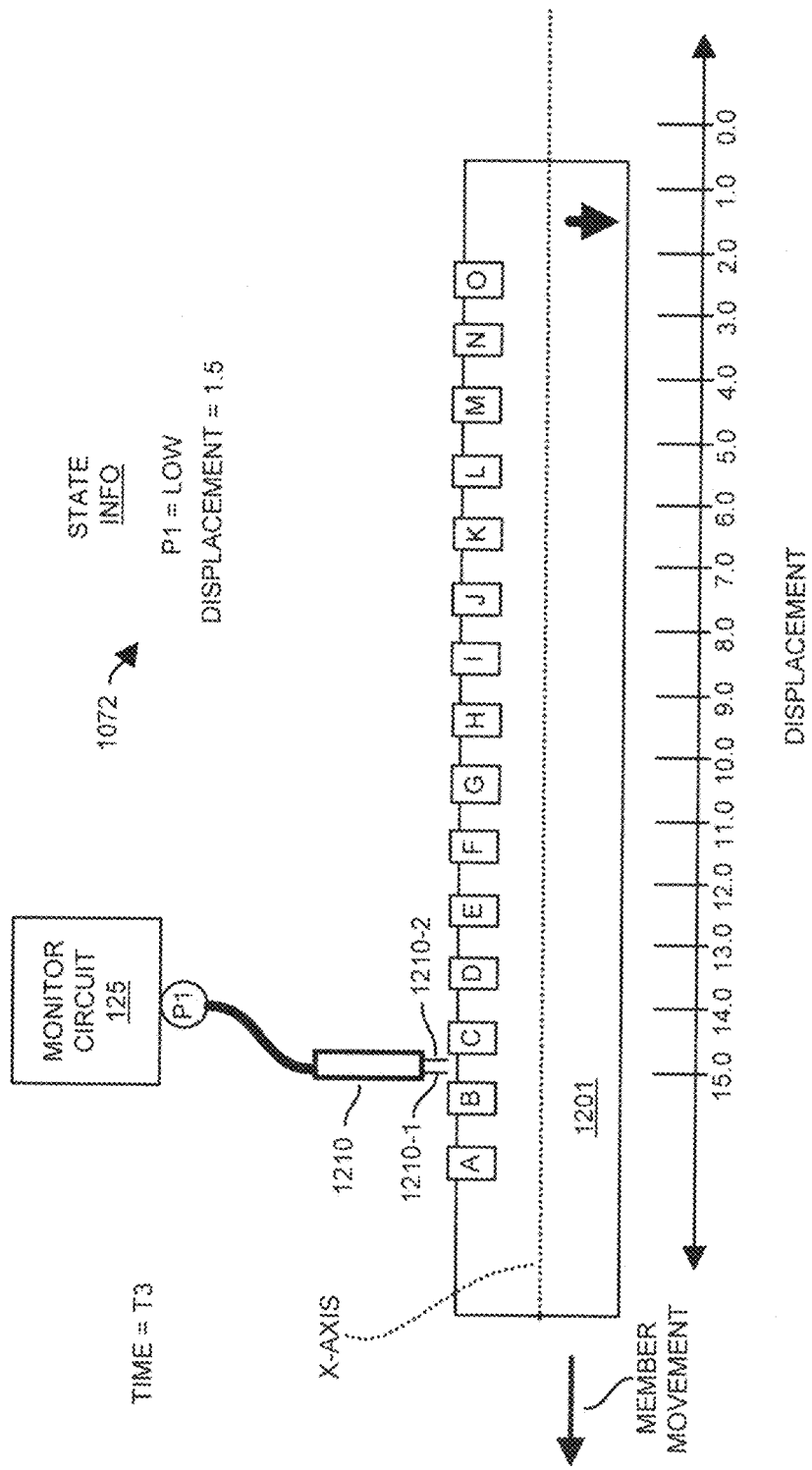

FIG. 15 is an example diagram illustrating detection of a position tracking element according to embodiments herein.

Based on movement of the member 1200 (core 1201) to the left along the x-axis, the member 1200 now has a position displacement of 1.5 units at time T3. In such an instance, both the probe element 1210-1 and the probe element 1210-2 of the probe 1210 contact a respective spacing between the position tracking element B and position tracking element C disposed on the member 1200 (core 1201). In such an instance, because no current flows through a respective position tracking element or respective probe elements, and because of the detected transition from a low resistance path provided by the position tracking element B to a high resistance path between probe element 1210-1 and 1210-2, the monitor circuit 125 produces the tracking information 1072 (including state information, LOW indicates absence of detection of a position tracking element) to indicate that the member 1200 is now at position equal to 1.5 at time T3.

In this manner, the monitor resource 125 tracks movement of member 1200 (and ots core 1201) over time.

FIGS. 16-23 are example side view diagrams illustrating measurement of displacement (position) based on sensing of position tracking elements according to embodiments herein.

Figure 16:
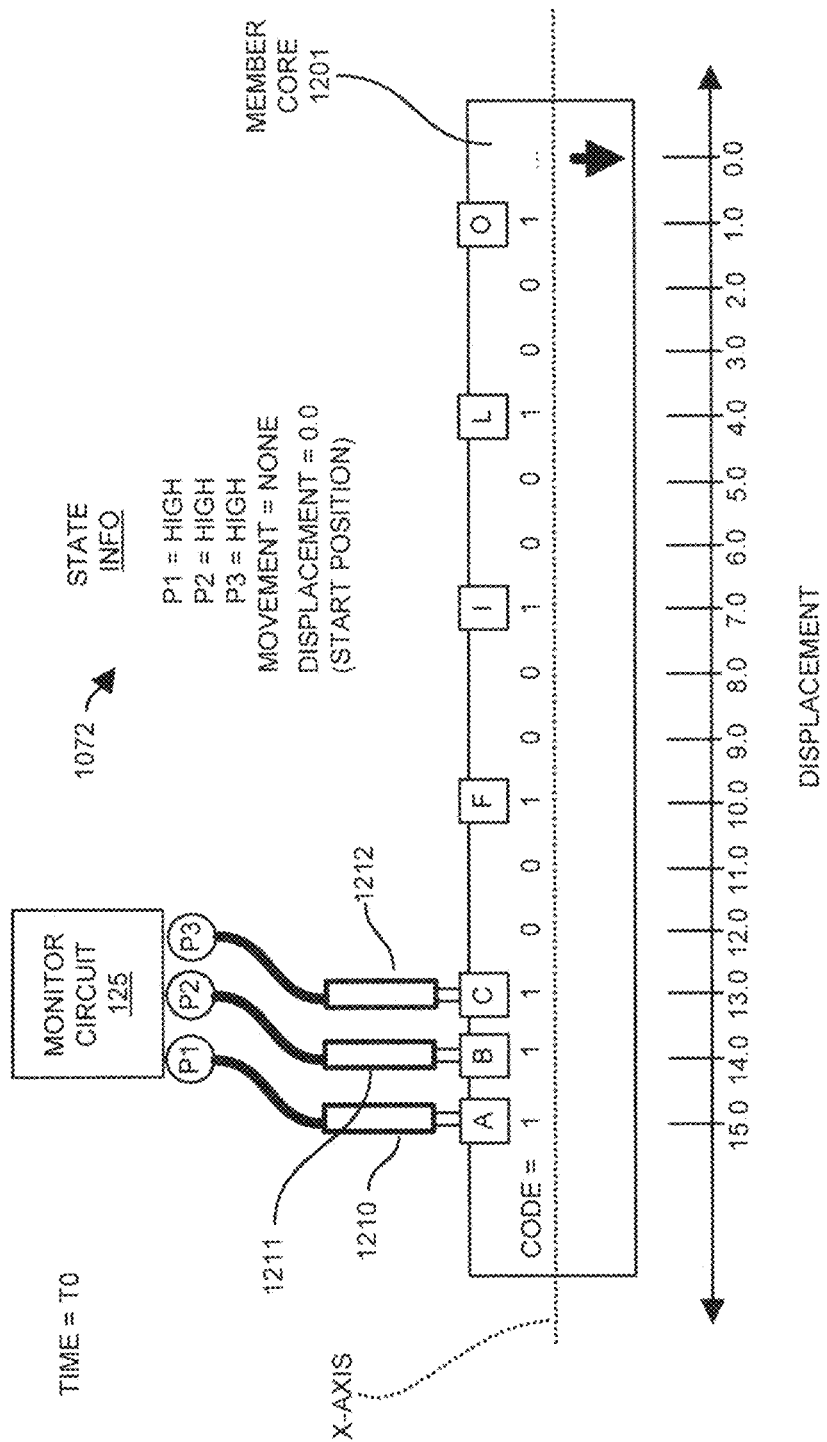
FIGS. 16-23 are example side view diagrams illustrating measurement of displacement (position) based on sensing of position tracking elements according to embodiments herein.

More specifically, FIG. 16 is an example diagram illustrating detection of a position and tracking according to embodiments herein.

In this example embodiment, the member 120 includes a coded sequence of position tracking elements monitored by a probe assembly.

For example, as shown, the coded sequence associated with sequence 1275-1 is 1 1 1 0 0 1 0 0 1 0 0 1 0 0 1 . . . A logic 1 in the code indicates presence of a position tracking element at a respective position of the member 1200; a logic 0 in the code indicates absence of a position tracking element a respective position of the member 1200.

In the coded sequence, position tracking element B is spaced apart from position tracking element A on the member core 1201 by one unit; position tracking element C is spaced apart from position tracking element B on the member core 1201 by one unit; position tracking element F is spaced apart from position tracking element C on the member core 1201 by three units; position tracking element I is spaced apart from position tracking element F on the member core 1201 by three units; position tracking element L is spaced apart from position tracking element I on the member core 1201 by three units; and so on.

As further shown, the probe assembly in FIG. 16 includes multiple probes (probe assembly) such as probe 1210, 1211, and 1212. Each of such probes is spaced apart by an amount (such as one unit of distance) in which the position tracking elements A, B, C, D, etc., are spaced apart from each other along axis X.

At its rightmost position (for example, starting position), the member 1200 has a position displacement of 0.0 units. In such an instance, in a similar manner as previously discussed, at time T0, the probe 1210 detects position tracking element A (low resistive path), the probe 1211 detects position tracking element B (low resistive path), the probe 1212 detects position tracking element C (low resistive path).

Because of the detected low resistance paths provided by the position tracking elements A, B, and C, the monitor circuit 125 produces the tracking information 1072 (including state information, probe P1=HIGH, probe P2=HIGH, probe P3=HIGH) to indicate that the member 1200 is disposed at displacement equal to 0.0 at time T0. Logic HIGH indicates detection of the respective position tracking element by a corresponding probe. That is, probe P1 (1210) detects position tracking element A; probe P2 (1211) detects position tracking element B; probe P3 (1212) detects position tracking element C.

Assume that the member 1200 moves to the left along the X-axis. Detection of the new position of the member 1200 is shown in FIG. 17.

Figure 17:
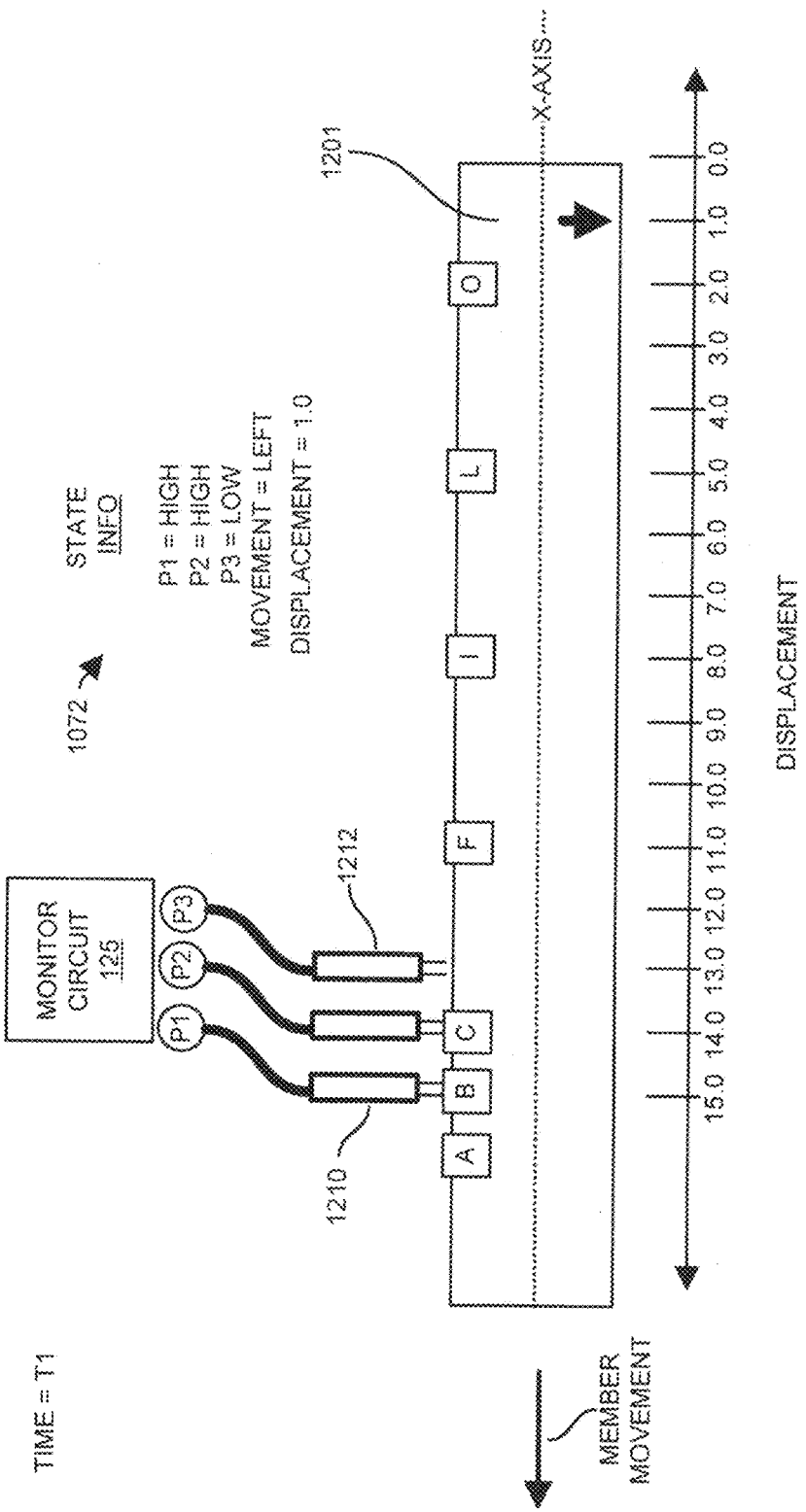

FIG. 17 is an example diagram illustrating tracking according to embodiments herein.

At time T1, the probe 1210 detects position tracking element B (low resistive path), the probe 1211 detects position tracking element C (low resistive path), the probe 1212 does not detect a position tracking element.

Because of the detected low resistance paths provided by the position tracking elements B, and C, the monitor circuit 125 produces the tracking information 1072 (including state information, probe P1=HIGH, probe P2=HIGH, probe P3=LOW) to indicate that the member 1200 is disposed at displacement equal to 1.0 at time T0. Again, logic HIGH indicates detection of the respective position tracking element. Logic LOW indicates absence of detecting a respective position tracking element.

Note that the monitor circuit records direction of movement of member 1200 (core 1201) to the left based on a change in detected settings associated with probes P1-P2-P3 from being HIGH-HIGH-HIGH at time T0 to being o HIGH-HIGH-LOW at time T1.

Assume that the member 1200 moves to the left along the X-axis. Detection of the new position of the member 1200 is shown in FIG. 18.

Figure 18:
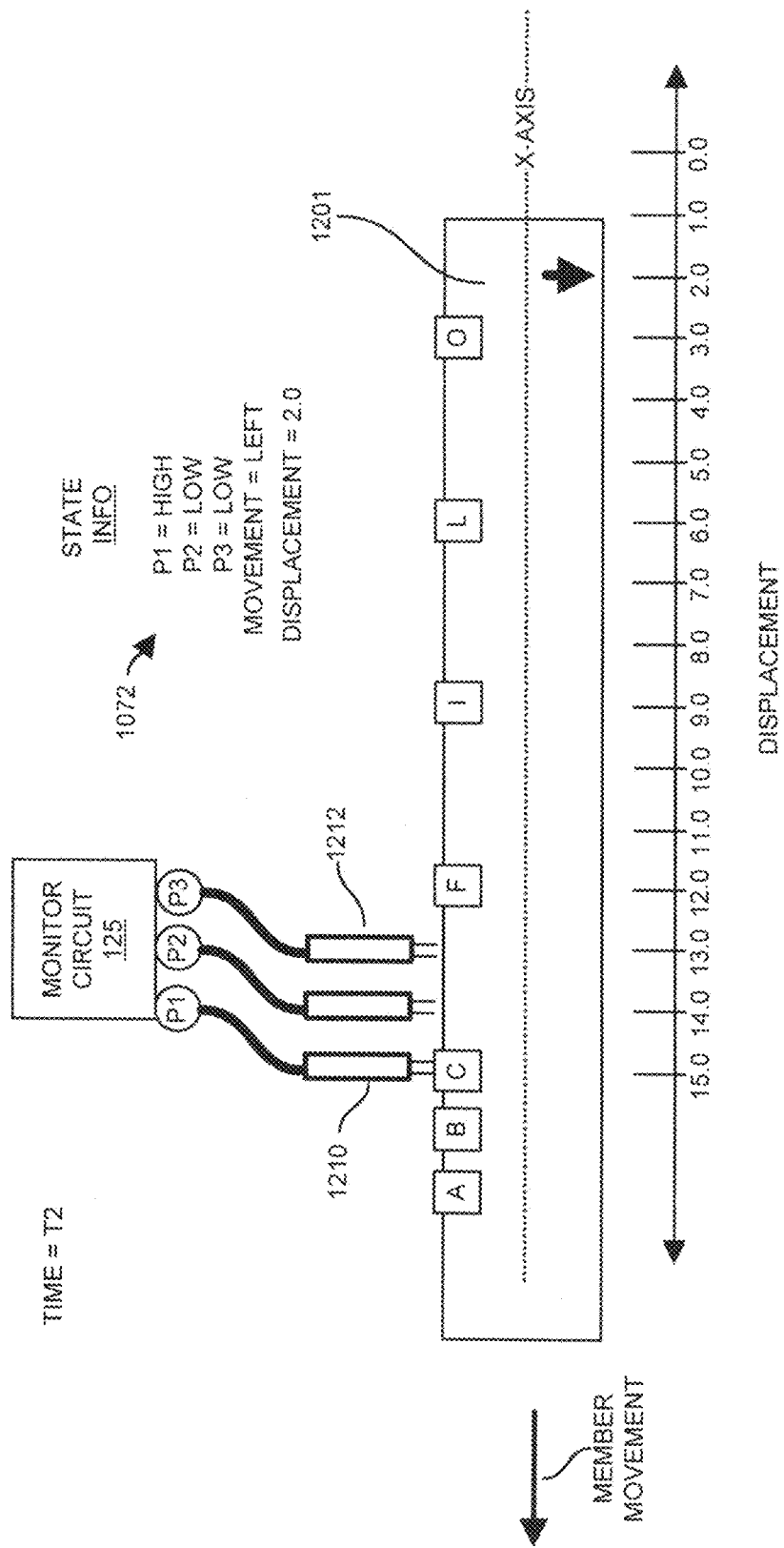

FIG. 18 is an example diagram illustrating detection of a position and tracking according to embodiments herein.

At time T2, the probe 1210 (P1) detects position tracking element C (low resistive path), the probe 1211 (P2) does not detect a position tracking element, the probe 1212 (P3) does not detect a position tracking element.

Because of the detected low resistance path provided by the position tracking element C, and absence of detecting position tracking elements, the monitor circuit 125 produces the tracking information 1072 (including state information, probe P1=HIGH, probe P2=LOW, probe P3=LOW) to indicate that the member 1200 is disposed at displacement equal to 2.0 at time T2. Again, logic HIGH indicates detection of the respective position tracking element. Logic LOW indicates absence of detecting a respective position tracking element.

Note that the monitor circuit records direction of movement of member 1200 to the left based on a change in detected settings associated with probes P1-P2-P3 from being HIGH-HIGH-LOW at time T1 to being HIGH-LOW-LOW at time T2.

Assume that the member 1200 moves to the left along the X-axis. Detection of the new position of the member 1200 is shown in FIG. 19.

Figure 19:
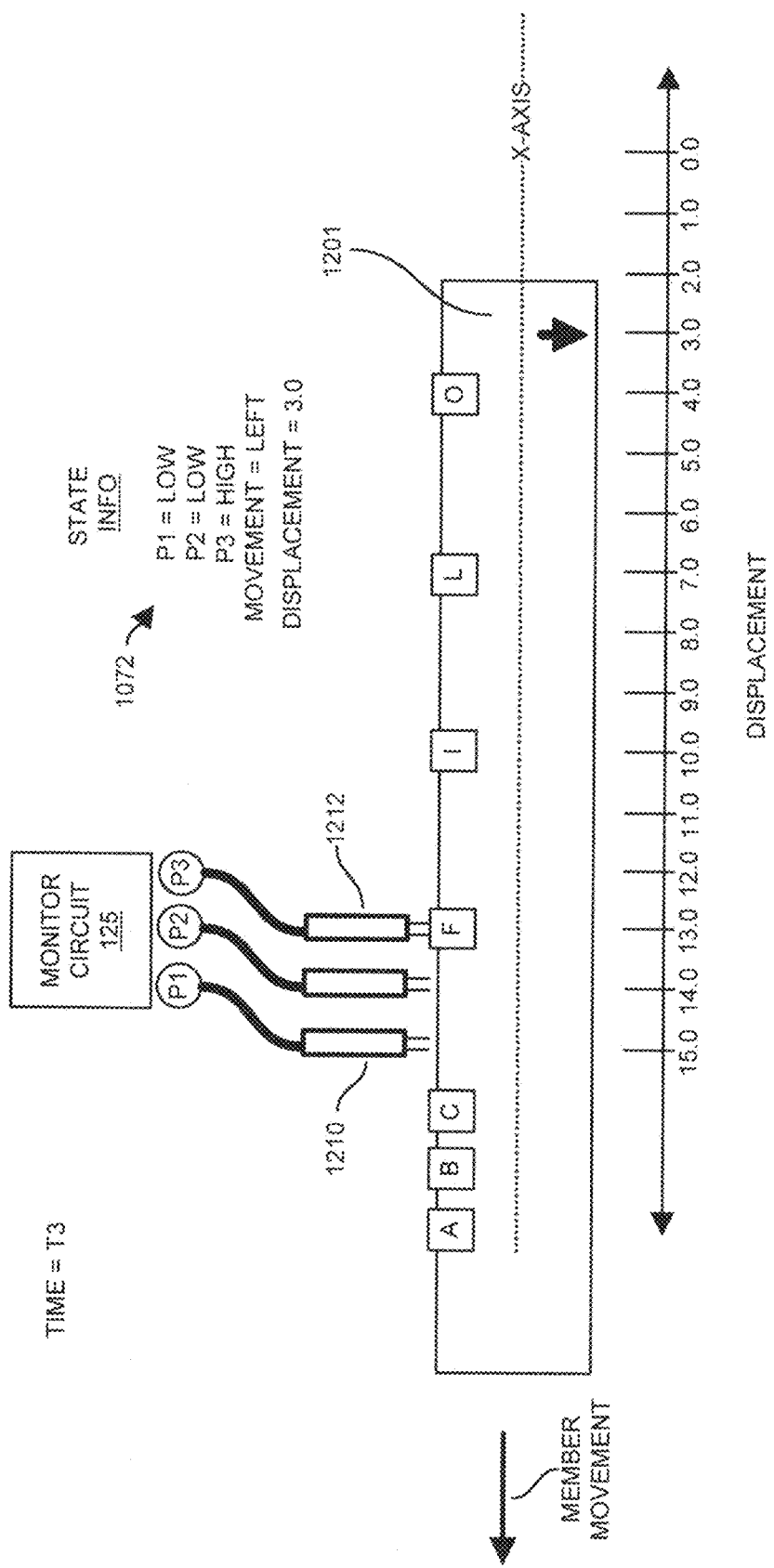

FIG. 19 is an example diagram illustrating detection of a position and tracking according to embodiments herein.

At time T3, the probe 1210 and probe 1211 do not detect a position tracking element, probe 1212 detects position tracking element F (low resistive path).

Because of the detected low resistance path provided by the position tracking element F, and absence of detecting position tracking elements, the monitor circuit 125 produces the tracking information 1072 (including state information, probe P1=LOW, probe P2=LOW, probe P3=HIGH) to indicate that the member 1200 (core 1201) is disposed at displacement equal to 3.0 at time T3. Again, logic HIGH indicates detection of the respective position tracking element. Logic LOW indicates absence of detecting a respective position tracking element.

Note that the monitor circuit records direction of movement of member 1200 to the left based on a change in detected settings associated with probes P1-P2-P3 from being HIGH-LOW-LOW at time T2 to being LOW-LOW-HIGH at time T3.

Assume that the member 1200 moves again to the left along the X-axis. Detection of the new position of the member 1200 is shown in FIG. 20.

Figure 20:
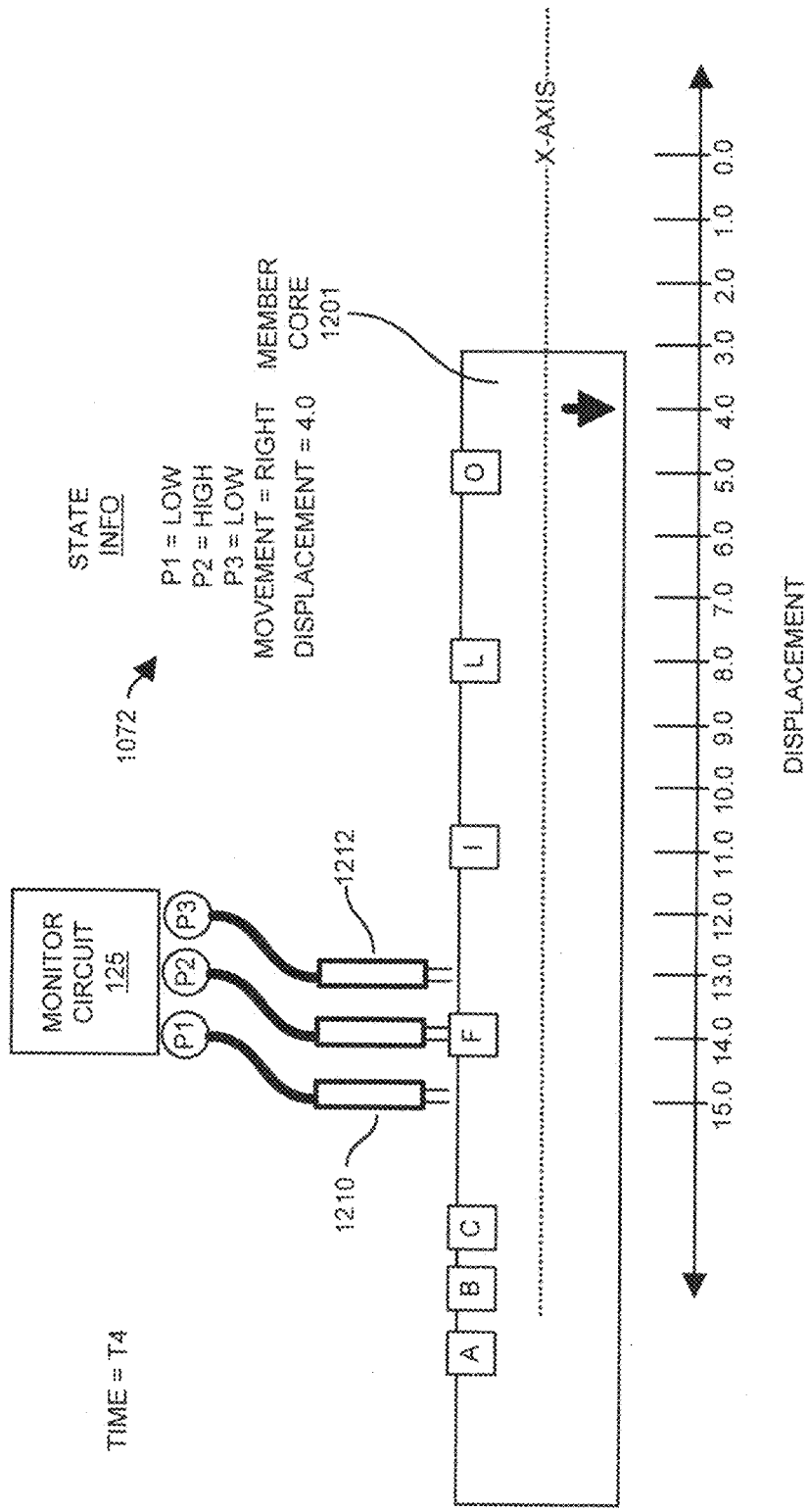

FIG. 20 is an example diagram illustrating detection of a position and tracking according to embodiments herein.

At time T4, the probe 1210 and probe 1212 do not detect a position tracking element, probe 1211 detects position tracking element F (low resistive path).

Because of the detected low resistance path provided by the position tracking element F, and absence of detecting position tracking elements, the monitor circuit 125 produces the tracking information 1072 (including state information, probe P1=LOW, probe P2=HIGH, probe P3=LOW) to indicate that the member 1200 is disposed at displacement equal to 4.0 at time T4. Again, logic HIGH indicates detection of the respective position tracking element. Logic LOW indicates absence of detecting a respective position tracking element.

Note that the monitor circuit 125 records direction of movement of member 1200 to the left based on a change in detected settings associated with probes P1-P2-P3 from being LOW-LOW-HIGH at time T3 to being LOW-HIGH-LOW at time T4.

Assume that the member 1200 moves to the right along the X-axis. Detection of the new position of the member 1200 is shown in FIG. 21.

Figure 21:
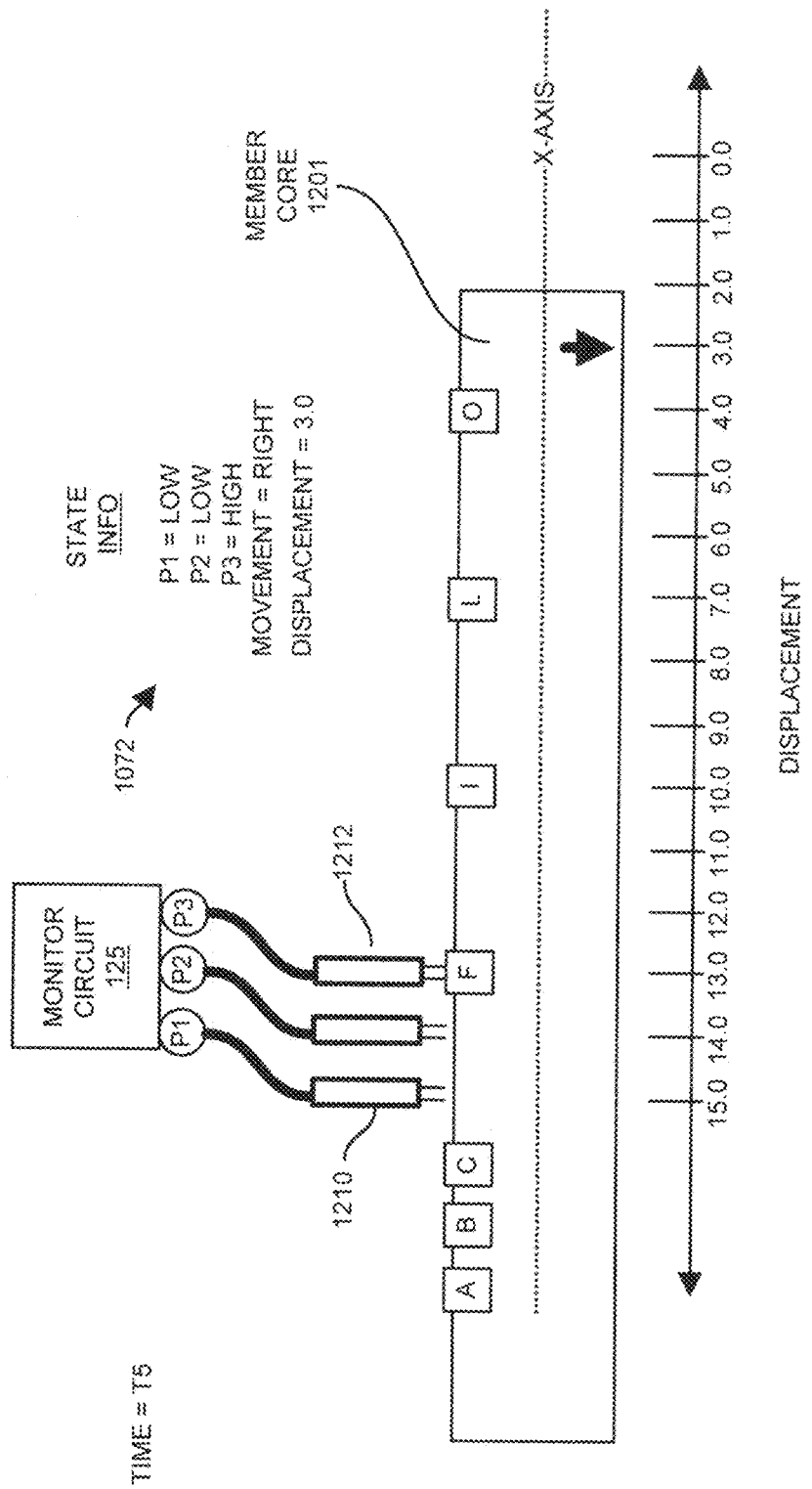

FIG. 21 is an example diagram illustrating detection of a position and tracking according to embodiments herein.

At time T5, the probe 1210 and probe 1211 do not detect a position tracking element, probe 1212 detects position tracking element F (low resistive path).

Because of the detected low resistance path provided by the position tracking element F, and absence of detecting position tracking elements, the monitor circuit 125 produces the tracking information 1072 (including state information, probe P1=LOW, probe P2=LOW, probe P3=HIGH) to indicate that the member 1200 is disposed at displacement equal to 3.0 at time T2. Again, logic HIGH indicates detection of the respective position tracking element. Logic LOW indicates absence of detecting a respective position tracking element.

Note that the monitor circuit notes and records direction of movement of member 1200 to the right based on a change in detected settings associated with probes P1-P2-P3 from being LOW-HIGH-LOW at time T4 to being LOW-LOW-HIGH at time T5. Monitor circuit 125 uses the coded sequence of position tracking elements as a basis to determine directional movement.

Assume that the member 1200 moves to the right along the X-axis. Detection of the new position of the member 1200 is shown in FIG. 22.

Figure 22:
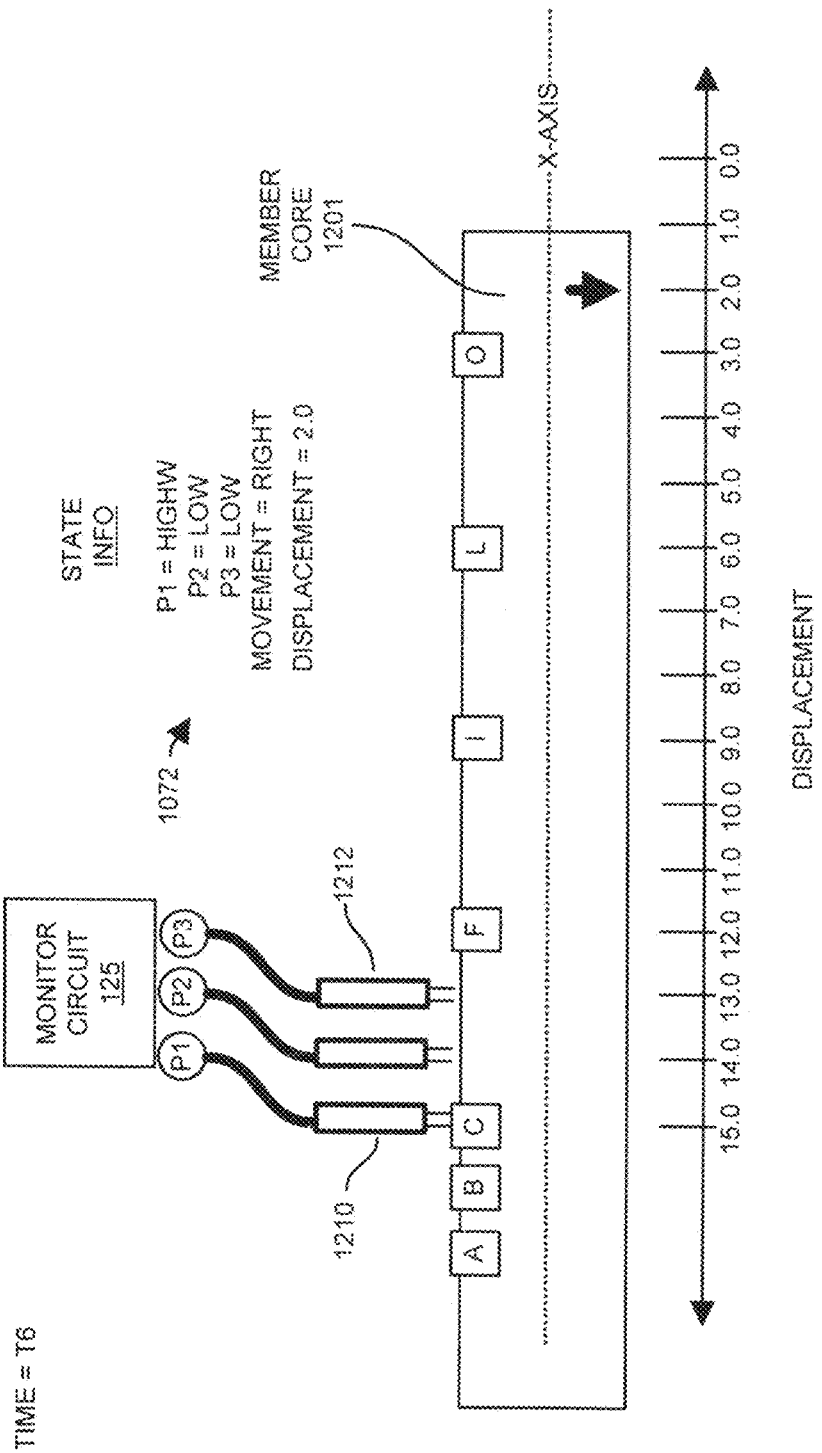

FIG. 22 is an example diagram illustrating detection of a position and tracking according to embodiments herein.

At time T6, the probe 1210 detects position tracking element C (low resistive path), the probe 1211 does not detect a position tracking element, the probe 1212 does not detect a position tracking element.

Because of the detected low resistance path provided by the position tracking element C, and absence of detecting position tracking elements, the monitor circuit 125 produces the tracking information 1072 (including state information, probe P1=HIGH, probe P2=LOW, probe P3=LOW) to indicate that the member 1200 is disposed at displacement equal to 2.0 at time T6. Again, logic HIGH indicates detection of the respective position tracking element. Logic LOW indicates absence of detecting a respective position tracking element.

Note that the monitor circuit records direction of movement of member 1200 (core 1201) to the right based on a change in detected settings associated with probes P1-P2-P3 from being LOW-LOW-HIGH at time T5 to being HIGH-LOW-LOW at time T6.

In this manner, because of the unique coding of position tracking elements on the member 1200, the monitor circuit is able to determine a direction of movement associated with the member from left-to-right or from right-to-left. For example, using time T6 as a reference, if the next state of detection associated with the probe assembly P1-P2-P3 is HIGH-HIGH-LOW, it is known by monitor circuit 125 that the member 1200 moved to the right by one unit; using time T6 as a reference, if the next state of detection associated with the probe assembly P1-P2-P3 is LOW-LOW-HIGH, it is known by the monitor circuit 125 that the member 1200 moved to the left by one unit based on knowing next possible states as indicated by the coded sequence 1275-1 (1 1 1 0 0 1 0 0 1 0 0 1 0 0 1 . . . ) as previously discussed.

Figure 23:
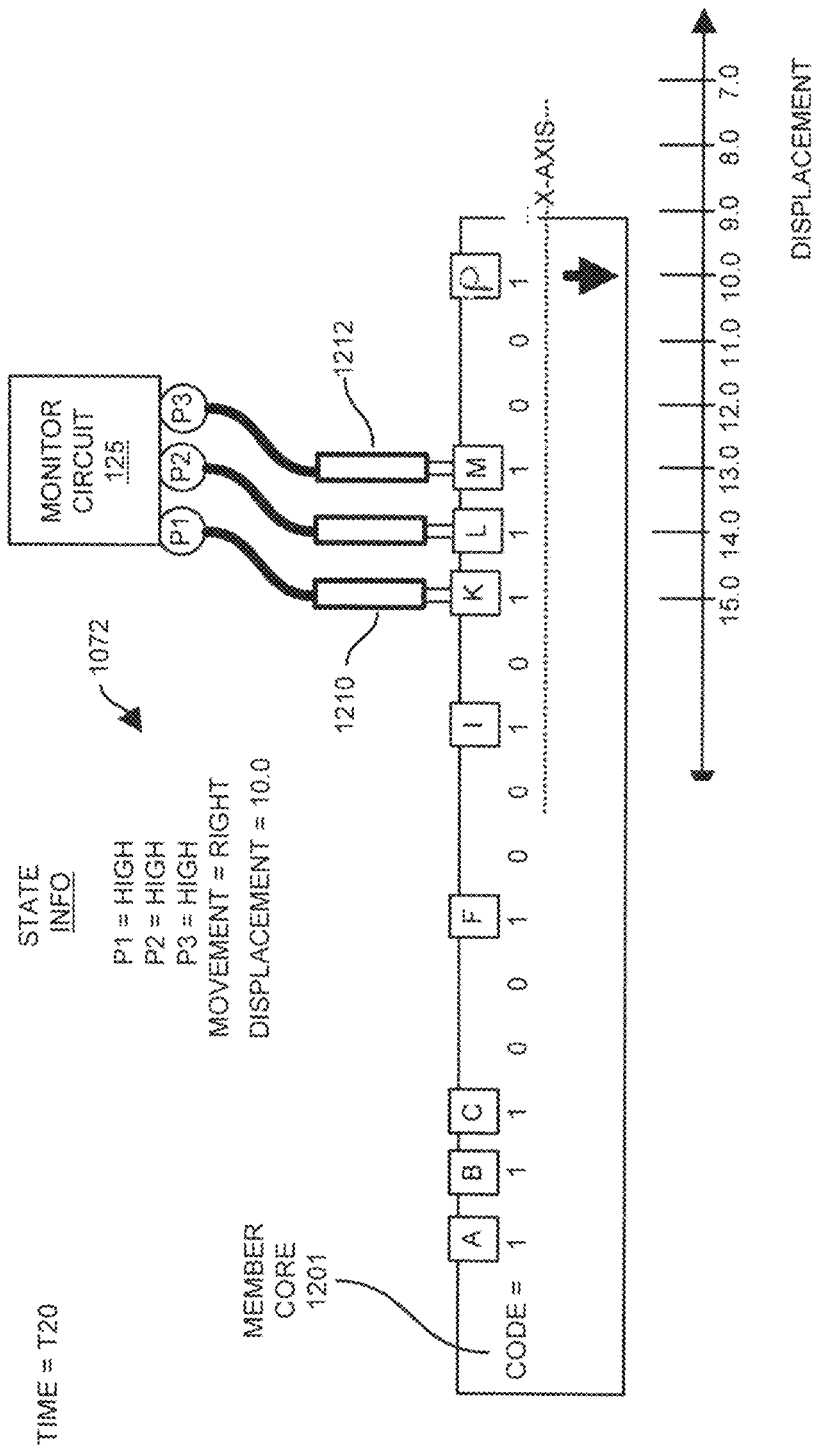

FIG. 23 is an example diagram illustrating coding of a sequence of position tracking elements according to embodiments herein.

In this example embodiment, 3 consecutive position tracking elements are present to mark every $10^{th}$ unit of distance displacement. For example, when the probe assembly P1-P2-P3 detects HIGH-HIGH-HIGH again at time T20, this indicates that the current position value recorded by the monitor resource 125 should be a multiple of ten. Otherwise, an error occurred associated with position tracking. Accordingly, the presence of a unique coded sequence of position tracking elements (such as presence of 3 position tracking elements K, L, M, in a row, spaced apart by one distance unit) provides a way to verify or confirm correctness of a current position setting.

Figure 24:
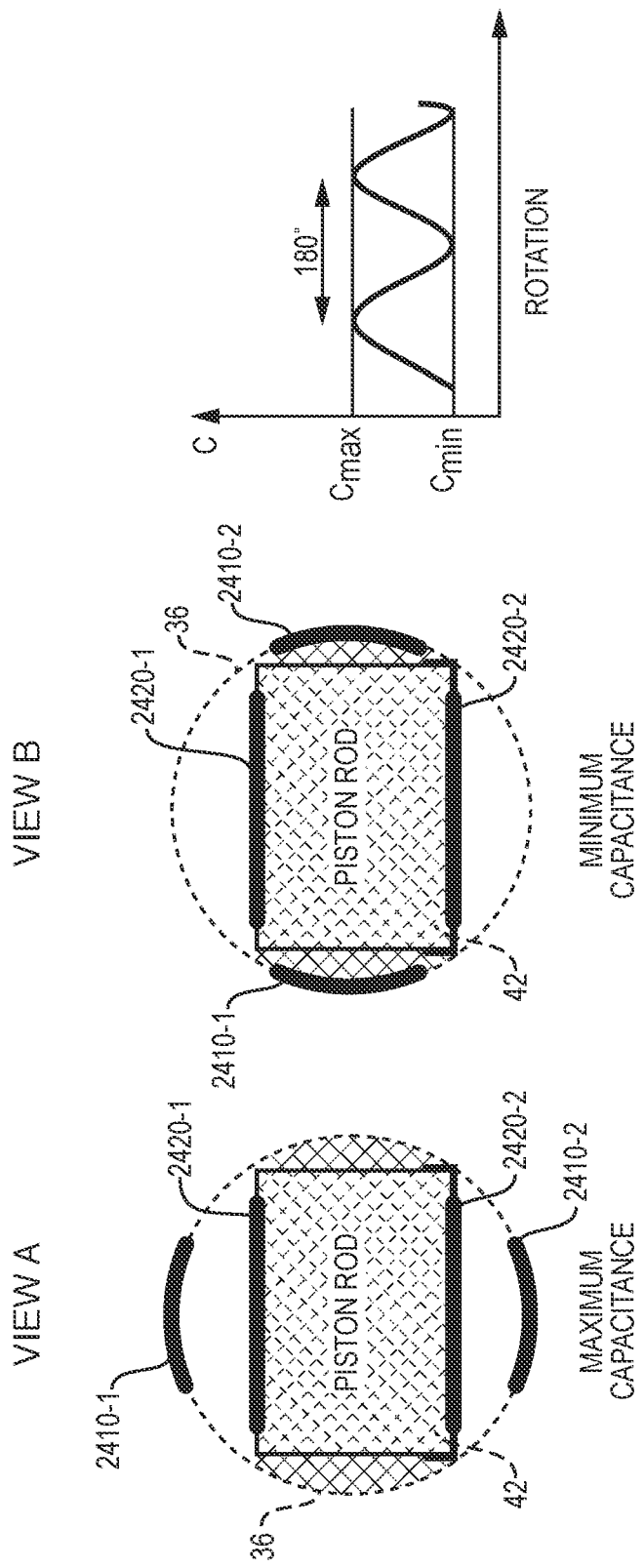
FIG. 24 is an example diagram illustrating capacitive sensing amendment corresponding determination of position according to embodiments herein.

FIG. 24 is an example diagram illustrating capacitive sensing of a position according to embodiments herein.

In addition to using linear motion to determine dose delivery, an alternative design may use rotary motion to measure rotational capacitance. For example, rotation of nut 36 relative to the piston rod 42 and uses a metal trace patterned (electrode 2420-1 and electrode 2420-2) along the length of the flat surfaces of piston rod 42. Two metal traces (electrode 2420-1 and electrode 2420-2) are printed 180 degrees apart on the nut 36, which rotates with respect to the piston rod 42.

As the nut 36 rotates relative to the piston rod, the detected capacitance between the two metal traces (electrode 2420-1 on the piston rod and electrode 2410-1 as well as electrode 2420-2 on the piston rod and electrode 2410-2 on the sleeve) varies from max (view A) to min (view B) as the sleeve rotates 90 degrees. Maximum capacitance (view A) is achieved each time the nut rotates 180 degrees and the two traces (electrodes) are aligned. Monitor circuit 125 monitors the capacitance change and counts the number of peak capacitance values determines the number of half rotations of the nut and this information can be used to determine the dose setting.

Since the nut rotates only during dose setting, and not during the injection process, this rotary design does not directly measure the piston translation and therefore is not a direct measure of the expelled medicament. However, this design could be used in conjunction with one of the above designs to directly measure the actual dose of medicament delivered.

Figure 25:
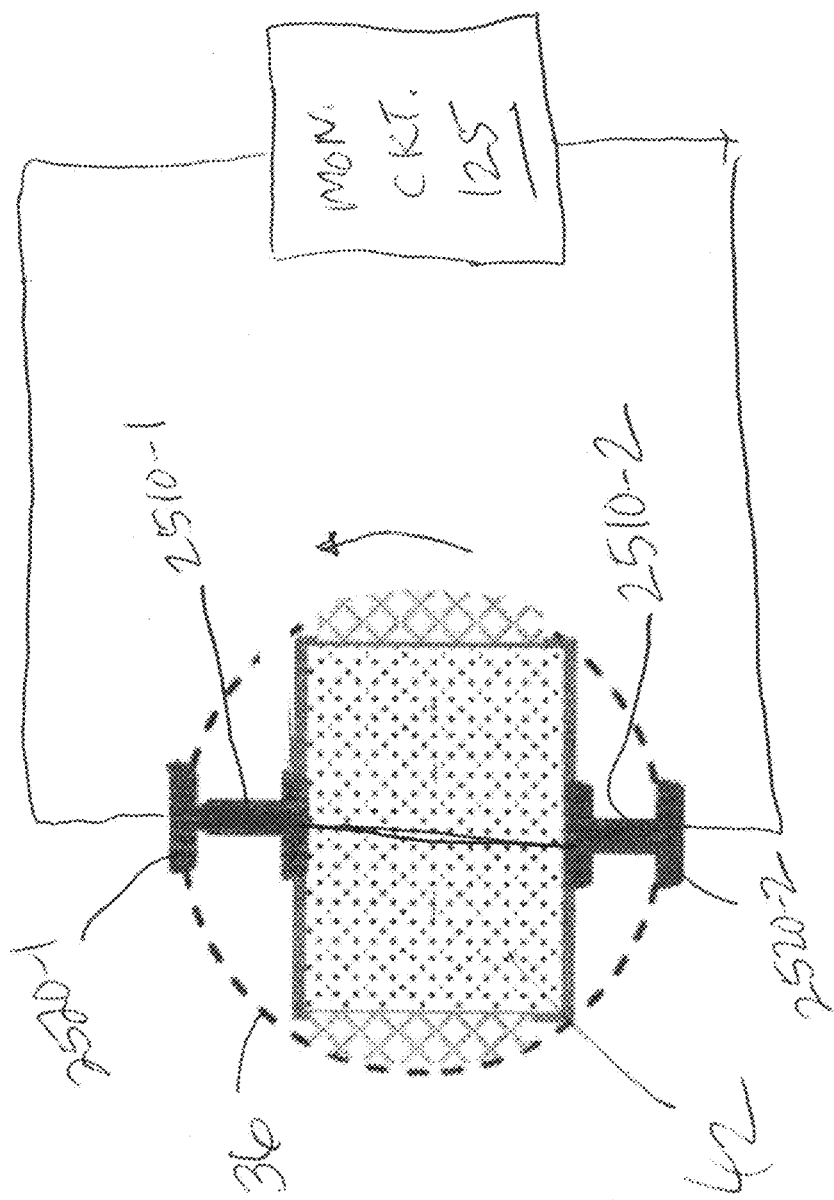
FIG. 25 is an example diagram illustrating contact sensing of a position according to embodiments herein.

FIG. 25 is an example diagram illustrating contact sensing of a position according to embodiments herein.

Another possible rotary design measures rotational electrical continuity. Electrode 2510-1 is electrically connected to electrode 2510-2. Such a design also measures nut 36 rotation relative to the piston rod 42, as described above, however, this design detects each 180 degrees rotation by measuring the presence of a current flowing through electrode 2520-1, through electrode 2510-1 and 2510-2, to electrode 2520-2 when a metal stub (2510-1 and 2510-2) on the piston rod 42 engages with respective electrical contacts (electrode 2520-1 and 2520-2) on the nut 36. As the rod 42 or nut rotates, the monitor circuit 125 detects a short circuit when electrode 2510-1 contacts electrode 2510-2 and electrode 2510-2 contacts electrode 2520-2. As the rod 42 or nut further rotates, the monitor circuit 125 detects an open circuit when electrode 2510-1 does not contact electrode 2510-2 and electrode 2510-2 does not contact electrode 2520-2.

Each completed (short) circuit represents 180 degrees of rotation of the nut 36 or rod 42.

In one embodiment, the stub 2510-1 is electrically coupled via a metal trace to stub 2510-2. Simultaneous physical contact of the stub 2510-1 to the electrode 2520-1 and physical contact of the stub 2510-2 and electrode 2520-2 produces a short circuit path detected by the monitor circuit 125. Rotation other than shown opens the circuit path and monitor circuit 125 detects the open circuit. As mentioned, each detected transition from open circuit to the short circuit path represents a 180 degree rotation.

In accordance with further embodiments, an electronic chip is inserted into the circuit between the trace of the rod 42 and the traces on the sleeve or nut that counts the number of completed circuits as a function of nut rotation around the piston rod. Counting the number of current pulses determines the number of half rotations of the nut and can determine the dose setting. As with the above rotary design, since the nut rotates only during dose setting this design does not directly measure the piston translation and therefore is not a direct measure of the expelled product. However, this design could be used in conjunction with one of the above designs to directly measure the actual dose of medicament delivered.

Referring again to FIG. 3, note that the function of the complete injection device 10 and the dose setting mechanism 30 according to this disclosure will now be described. Injection device 10 is provided to a user with or without the cartridge 8 of medicament positioned within the cartridge holder 2. If the injection device 10 is configured as a reusable device, then cartridge holder 2 is connected to housing 3 of the dose setting mechanism 30 in a releasable and reusable manner. This allows the user to replace the cartridge with a new full cartridge when all the medicament is expelled or injected from the cartridge. If the device is configured as a disposable injection device, then the cartridge of medicament is not replaceable because the connection between the cartridge holder 2 and the housing 3 is permanent. Only through breaking or deformation of this connection can the cartridge be removed from the injection device. Such a disposable device is designed to be thrown out once the medicament has been expelled from the cartridge.

The user first removes the cap 1 from the device and installs an appropriate pen needle 4 to the cartridge holder 2 using connector 7. If the device is not pre-primed during the device assembly, or does not have an automatic or forced priming feature, then the user will need to manually prime the device as follows. The dose knob 31 is rotated such that a first dose stop is reached, which corresponds to a predetermined small fixed dose of medicament.

The injection device 10 of this disclosure can also have a so-called forced or automatic priming feature. Prior to using the dose setting mechanism, i.e., before a user could dial one of the predetermined fixed dose setting, a sliding lock would necessarily need to pushed in the proximal direction such that is moves distally relative to the dose knob. This axial movement forms an irreversible locking relationship between the dose knob and the distal end of the clutch. This locking relationship also causes the dose knob and clutch to be rotationally fixed to each other. Before the sliding lock is engaged with the clutch, the clutch can be rotated, which also causes rotation of the nut, to cause the piston rod 42 to move axially relative to the housing. The clutch is rotated until a visual observation and/or tactile notification indicates that the foot 42a located on the piston rod 42 is in firm abutment with distal facing surface of the sliding piston 9. This abutment between the foot and the sliding piston will ensure that an accurate dialed dose will be delivered out of the needle cannula. This rotation of the clutch is preferably performed during the assembly of the injection device and likewise after ensuring abutment of the foot with the sliding piston 9, the manufacturing process would cause the sliding lock to be pushed to the final, locked position.

Returning to the priming procedure, once the priming stop is reached, the user may need to cancel the priming procedure and can do so by using the dose canceling procedure. This cancellation procedure also applies to any dose setting. Dose cancellation is accomplished by turning the dose knob in the opposite direction and will generate a notification that can be the same or different as the dose setting notification and/or dose delivery notification. Because the snap element 33 is rotationally fixed to the dose sleeve 38, and the dose sleeve is threaded engaged to the inner surface of housing 3, rotation of the dose knob during dose setting and dose cancellation causes relative rotation between the dose sleeve and the housing. The threaded connection between the housing and the dose sleeve causes the dose sleeve, snap element, clutch, and dose knob to translate axially as the dose knob is rotated. During dose cancellation, these components rotate and translate axially in the opposite or proximal direction.

Rotation of the dose knob also causes rotation of nut 36 about threads 60 on the outer surface of piston rod 42, which does not rotate and remains axially fixed relative to the housing 3 because of relative pitch differences in the threaded parts as explained above. The rotation of the nut relative to the stationary piston rod, which is supported by its contact with the sliding piston, causes the nut to translate or climb up the piston rod in the distal direction. A reverse rotation during dose cancellation causes the nut to translate in the reverse direction relative to piston rod. The distance traveled by the nut to achieve the desired dose setting is directly proportional to an amount of medicament that would be expelled if the dose delivery procedure were initiated and completed. Because the pitch of the threaded connection between the dose sleeve and the housing is greater than pitch of the threads on the nut, the dose sleeve, snap element, clutch and dose knob will travel a greater axial distance than the nut as it climbs up or down the piston rod. The difference in axial movement would normally bind the dose setting mechanism, but does not do so because the difference in pitch is compensated for by the sliding splined connection between the nut and the clutch, thus allowing the clutch to travel axially a greater distance longitudinally than the nut. During injection, the clutch pushes on the snap element and as such on the dose sleeve. This axial force causes the dose sleeve to turn due to the thread to the body. The dose sleeve will only start to turn when it is pushed, if the pitch of the thread is high enough. If the pitch is too low the pushing will not cause rotation because the low pitch thread becomes what is called a "self-locking thread."

Rotation of the dose knob also causes rotation of the driver because of the splined rotationally fixed connection to the dose sleeve. Since the torsion spring 90 is fixed at one end to the driver and at the other end to the piston guide, which in turn is fixed axially and rotationally to the housing, the torsion spring is wound up increasing in tension during dose setting. As mentioned, the torque of the tension spring exerts a counter rotational force on the dose sleeve. Preferably during assembly of the dose setting mechanism, the torsion spring is pre-tensioned so that even at the zero dose condition the torsion spring exerts a counter rotational force on the dose sleeve. The counter rotation force provides a first fail-safe feature of the dose setting mechanism. This first fail-safe mechanism prevents a user from setting a dose that is not one of the finite set of predetermined dose settings. In other words, if a user is rotating the dose knob such that it is between two dose stops, or between the zero dose hard stop and a first dose stop or a priming stop, and the user releases the dose knob, the counter rotational force of the torsion spring will return the protrusion to the last engaged dose stop or to the zero dose hard stop. Additionally, during a dose cancellation procedure the counter rotational force will assist the user in rotating the dose knob back down to the next lower fixed dose setting or possibly all the way back to the zero dose setting.

During dose setting, the dose knob 31 translates out and away from the distal end of housing 3. As the dose sleeve 38 rotates and translates, the progress of the dose setting (or dose cancellation) is observed in window 3a of housing 3 as the printed indicia 40 on the dose sleeve moves past the open window. When a desired predetermined dose setting is reached the indicia for that dose will appear in the window. At this point the injection device 10 is ready for a priming procedure or, if already primed, the delivery of the medicament to an injection site. In either the case, the user will push on the dose knob in the proximal direction until the zero dose hard stop is reached and a zero dose indicia is observed in the window. During a priming step the user will observe whether medicament is expelled out of the cannula 6 of pen needle 4. If no medicament is expelled this means the piston foot 42a is not in abutment with the distal surface of sliding piston 9. The priming step is then repeated until medicament is observed exiting the cannula.

The dose setting mechanism of the present disclosure can also have a maximum dose hard stop feature that prevents a user from setting a dose greater than the highest predetermined dose setting.

Once the dose setting mechanism is primed, the user then selects and sets a desired fixed dose by repeating the same steps used for priming except that the dose knob will be rotated past the priming stop until the appropriate dose stop is and the desired dose value appears in the window 3a. In some cases, it is preferred to have no indicia show in the window when dialing between predetermined dose settings, while in other cases it is desirable to show an indicia in the window that is indicative of a non-settable dose position between the fixed dose settings.

Once one of the predetermined dose settings has been dialed on the dose setting mechanism, the user can then exert an axial force in the proximal direction to initiate the dose delivery procedure. The axial force exerted by the user overcomes the distally directed force exerted by the second biasing member 91 causing the dose knob 31, clutch 32 and dose selector 35 to move axially in the proximal direction relative to the snap element 33 and housing 3. This initial movement rotationally fixes the clutch and dose knob to the housing through the splined connection between the floating spline 34 and splines inside dose selector 35. The splined connection between the dose selector and floating spline 34 remains engaged during dose setting and during dose delivery even though the dose selector 35 moves axially with the dose knob 31 and relative to the floating spline 34.

As the user maintains the axial force on both the dose knob 31 and the dose button 72 during the continuation of the dose delivery procedure, the clutch 32 will abut the distal end of the snap element causing it to move axially in the proximal direction. The clutch pushes on the snap element. The snap element is fixed to the dose sleeve, so the clutch pushes on the dose sleeve. As the dose sleeve has a thread with a sufficiently high pitch relative to the body, the axial force on the dose sleeve will cause the dose sleeve and as such the snap element to turn relative to the body, and by turning relative to the body it moves in the proximal direction. The dose selector slides into the housing but does not rotate relative to the housing 3 due to the splined engagement with the housing. The rotation of the dose sleeve 38 also causes rotation of the driver 41 into the threaded connection with piston guide 43, which drives the piston rod proximally and results in a concurrent de-tensioning of torsion spring 90. The driver does not directly drive the piston rod. As the driver rotates, the driver moves in the proximal direction and pushes the nut forwards. As the nut doesn't turn, the driver pushes the nut and the piston rod forward.

The nut 36 does not rotate during dose delivery because of the rotationally fixed relationship with clutch 32 that is rotationally fixed to the housing through rotationally fixed relationship of the dose knob, floating spline and the housing. The nut therefore can only move axially carrying the piston rod 42 with it because the piston rod is prevented from rotating by the non-circular opening 64 engaged with the flats 203 on the piston rod. The piston rod is moved axially the same distance that the nut originally translated relative to the piston rod during dose setting. Again, this movement of the piston rod can be determined through the electrical conductivity measurement or by digitally counting conductive traces or stripes as described above. This axial movement without rotation is caused by the rotational and axial movement of the proximal end of the driver in abutment with a flange 36a on nut 36. Axial movement of the piston rod causes the sliding piston 9 to also move axially relative to the inside walls of the stationary cartridge 8 forcing an amount of medicament out of the needle cannula 6 that is equivalent to the predetermined fixed dose that was set during the dose setting procedure.

If the user stops or halts the dose delivery procedure by removing the axial force on the dose knob a fail-safe mechanism is activated. Removal of the axial force causes the compression spring 91 to bias the dose knob in the distal direction. If the user halts the dose delivery between two predetermined fixed dose settings, then the dose knob and the axially fixed dose selector will both be prevented from moving proximally because of a projecting rib inside the dose selector that will stop the axially movement of dose selector and dose knob. Without this projecting rib, the dose selector would move distally such that the dose knob would re-engage with the snap element, thus placing the dose knob, clutch and nut back into rotational engagement with the snap element. The torque exerted on the snap element through the driver would then counter rotate the nut, thus reducing the set dose by an unknown amount. This counter rotation would continue until the next lowest predetermined fixed dose setting is reached, where the corresponding dose stop would stop the counter rotation. Therefore, a resumption of the halted dose delivery procedure will continue without any unknown decrease in the set dose, thus allowing the originally set predetermined dose to be delivered. A halted dose delivery could be determined using the electrical circuits described above because the measuring device would sense a rate change of resistance or time lag between conductive readings. Likewise, a halted dose delivery could be determined and recorded by using a clock function of the measuring device that would sense no change of resistance over a period of time for the injection corresponding to the halted injection.

It is to be understood that the embodiments described above and shown in the drawings are to be regarded only as non-limiting examples of the possible designs of the safety assembly and such designs may be modified in many ways within the scope of the patent claims.

Figure 26:
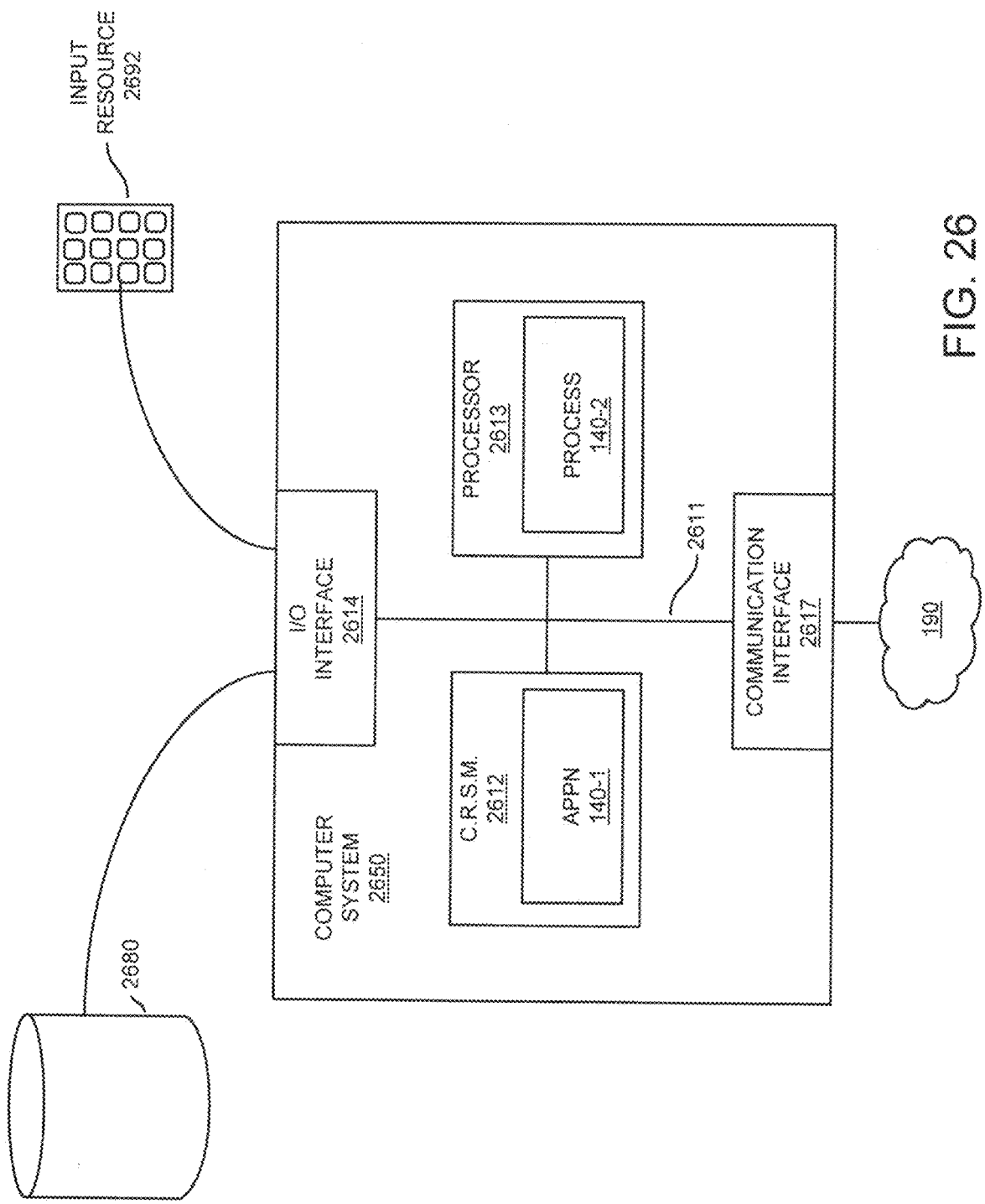
FIG. 26 is an example diagram illustrating computer architecture implementing one or more methods according to embodiments herein.

FIG. 26 is an example diagram illustrating computer architecture implementing one or more methods according to embodiments herein.

Note that any of the resources (such as fabrication manager that fabricates the position tracking system, monitor resource, position tracking management, etc.) as discussed herein can be configured to include computer processor hardware and corresponding executable instructions to carry out the different operations as discussed herein.

As shown, computer system 2650 of the present example can include an interconnect 2611 that couples computer readable storage media 2612 such as a non-transitory type of media (such as a type of hardware storage medium) in which digital information can be stored and retrieved, a processor 2613, I/O interface 2614, and a communications interface 2617.

I/O interface 2614 supports connectivity to repository 2680 and input resource 2692.

Computer readable storage medium 2612 can be any hardware storage device such as memory, optical storage, hard drive, floppy disk, etc. In one embodiment, the computer readable storage medium 2612 stores instructions and/or data.

As shown, computer readable storage media 2612 can be encoded with management application 140-1 (e.g., including instructions) to carry out any of the operations as discussed herein.

During operation of one embodiment, processor 2613 accesses computer readable storage media 2612 via the use of interconnect 2611 in order to launch, run, execute, interpret or otherwise perform the instructions in management application 140-1 stored on computer readable storage medium 2612. Execution of the management application 140-1 produces management process 140-2 to carry out any of the operations and/or processes as discussed herein.

Those skilled in the art will understand that the computer system 2650 can include other processes and/or software and hardware components, such as an operating system that controls allocation and use of hardware resources to management application 140-1.

In accordance with different embodiments, note that computer system 2650 may be or included in any of various types of devices, including, but not limited to, a mobile computer, user equipment, a personal computer system, a wireless device, base station, phone device, desktop computer, laptop, notebook, netbook computer, mainframe computer system, handheld computer, workstation, network computer, application server, storage device, a consumer electronics device such as a camera, camcorder, set top box, mobile device, video game console, handheld video game device, a peripheral device such as a switch, modem, router, set-top box, content management device, handheld remote control device, any type of computing or electronic device, etc. The computer system 2650 may reside at any location or can be included in any suitable resource in any network environment to implement functionality as discussed herein.

Functionality supported by the different resources will now be discussed via flowcharts in FIGS. 27 and 28. Note that the steps in the flowcharts below can be executed in any suitable order.

Figure 27:
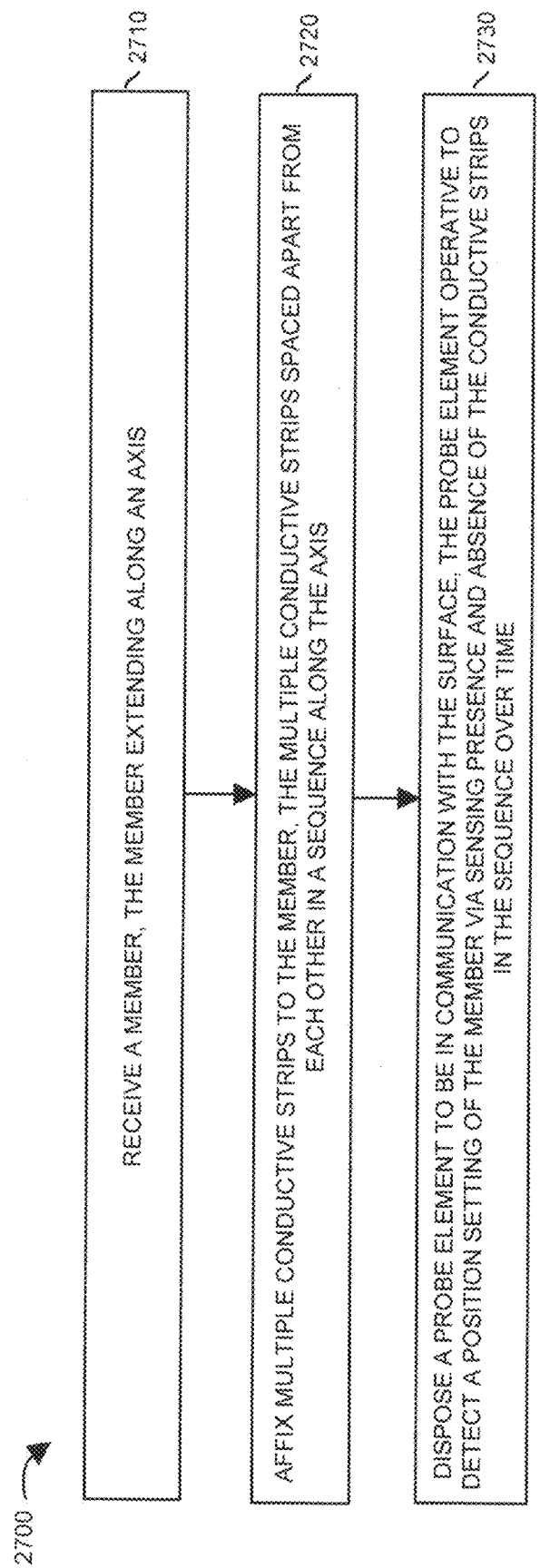
FIG. 27 is an example diagram illustrating a fabrication method according to embodiments herein.

FIG. 27 is a flowchart 2700 illustrating an example method according to embodiments herein. Note that there will be some overlap with respect to concepts as discussed above.

In processing operation 2710, a fabrication system (such as computer system 2650) according to embodiments herein receives a member, the member extending along a lengthwise axis.

In processing operation 2720, the fabrication system fabricates multiple position tracking elements (such as conductive strips) on the member; the multiple position tracking elements are spaced apart from each other in a sequence along the lengthwise axis.

In processing operation 2730, the fabrication system disposes a probe element to be in communication with the member, the probe element operative to detect a position setting of the member via sensing presence and absence of the position tracking elements in the sequence over time.

Figure 28:
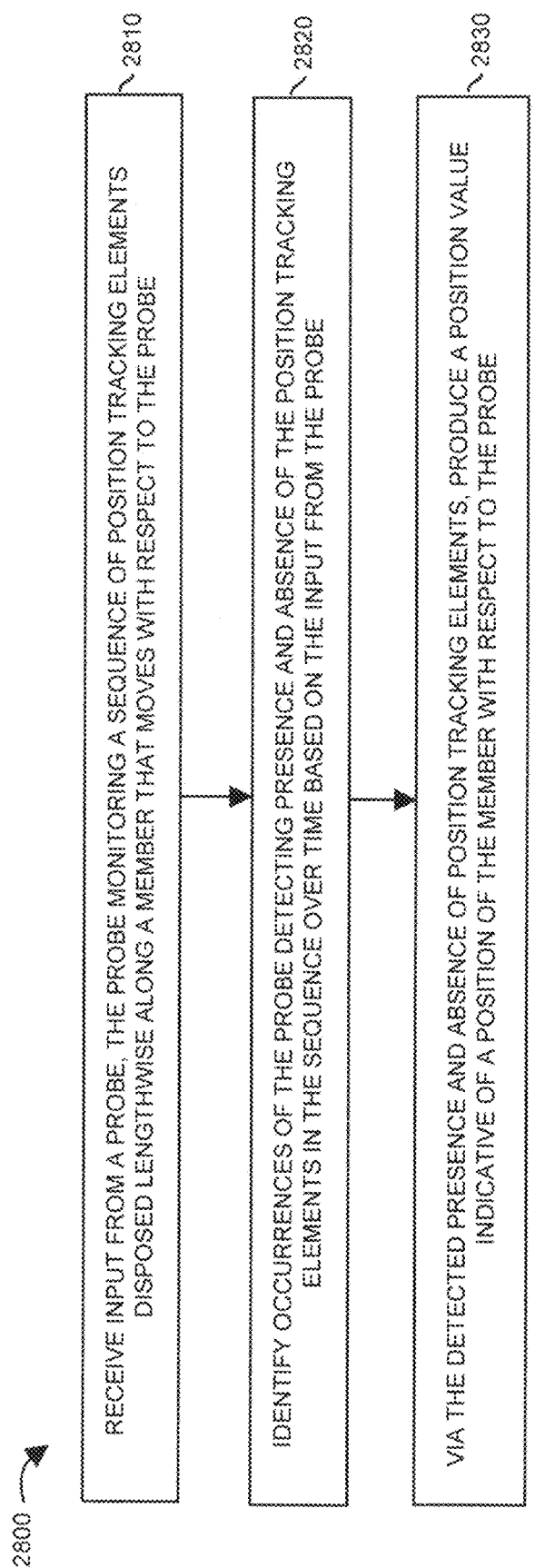
FIG. 28 is an example method illustrating functionality associated with a position tracking system according to embodiments herein.

FIG. 28 is a flowchart 2800 illustrating an example method according to embodiments herein. Note that there will be some overlap with respect to concepts as discussed above.

In processing operation 2810, the monitor resource 125 receives input from a probe, the probe monitoring a sequence 1275 of position tracking elements disposed lengthwise along a member that moves with respect to the probe.

In processing operation 2820, the monitor circuit identifies occurrences of the probe detecting presence and absence of the position tracking elements in the sequence over time based on the input from the probe.

In processing operation 2830, via the detected presence and absence of position tracking elements, the monitor resource 125 (such as circuit) produces a position value indicative of a position of the member with respect to the probe.

Note again that techniques as discussed herein are well suited for use in applications supporting dynamic control of a radiation pattern. However, it should be noted that embodiments herein are not limited to use in such applications and that the techniques discussed herein are well suited for other applications as well.

Based on the description set forth herein, numerous specific details have been set forth to provide a thorough understanding of claimed subject matter. However, it will be understood by those skilled in the art that claimed subject matter may be practiced without these specific details. In other instances, methods, apparatuses, systems, etc., that would be known by one of ordinary skill have not been described in detail so as not to obscure claimed subject matter. Some portions of the detailed description have been presented in terms of algorithms or symbolic representations of operations on data bits or binary digital signals stored within a computing system memory, such as a computer memory. These algorithmic descriptions or representations are examples of techniques used by those of ordinary skill in the data processing arts to convey the substance of their work to others skilled in the art. An algorithm as described herein, and generally, is considered to be a self-consistent sequence of operations or similar processing leading to a desired result. In this context, operations or processing involve physical manipulation of physical quantities. Typically, although not necessarily, such quantities may take the form of electrical or magnetic signals capable of being stored, transferred, combined, compared or otherwise manipulated. It has been convenient at times, principally for reasons of common usage, to refer to such signals as bits, data, values, elements, symbols, characters, terms, numbers, numerals or the like. It should be understood, however, that all of these and similar terms are to be associated with appropriate physical quantities and are merely convenient labels.

While this invention has been particularly shown and described with references to preferred embodiments thereof, it will be understood by those skilled in the art that various changes in form and details may be made therein without departing from the spirit and scope of the present application as defined by the appended claims. Such variations are intended to be covered by the scope of this present application. As such, the foregoing description of embodiments of the present application is not intended to be limiting. Rather, any limitations to the invention are presented in the following claims.

We claim:

1. An apparatus comprising:
a member extending along an axis;
multiple conductive strips including a first sequence of conductive strips disposed on a surface of the member and a second sequence of conductive strips disposed on the surface of the member, the conductive strips in the first sequence of spaced apart from each other along the axis, the conductive strips in the second sequence spaced apart from each other along the axis;
probe elements, the probe elements in contact with the first sequence of conductive strips and the second sequence of conductive strips over time, the probe elements operative to detect a position setting of the member via sensing presence of the conductive strips in the first sequence and the second sequence over time;
wherein the probe elements include a first probe element and a second probe element;
the first probe element in communication with the first sequence and operative to detect presence of the conductive strips in the first sequence over time;
the second probe element in communication with the second sequence and operative to detect presence of the conductive strips in the second sequence over time;
the apparatus further comprising a third sequence of conductive strips disposed on the surface of the member. the conductive strips in the third sequence spaced apart from each other along the axis; and
wherein the probe elements include a third probe element, the third probe element in communication with the third sequence and operative to detect presence of the conductive strips in the third sequence over time.

2. The apparatus as in claim 1, wherein the conductive strips in the first sequence are disposed in an orthogonal manner with respect to the axis of the member.

3. The apparatus as in claim 1 further comprising:
threads disposed on the surface of the member, the threads spiraling on the surface about the member along the axis.

4. An apparatus comprising:
a member extending along an axis;
multiple conductive strips disposed on a surface of the member, the multiple conductive strips spaced apart from each other in a sequence along the axis;
a probe element, the probe element in communication with the multiple conductive strips in the sequence over time, the probe element operative to detect a position setting of the member via sensing presence of the conductive strips in the sequence over time;
threads disposed on the surface of the member, the threads spiraling on the surface about the member along the axis; and
wherein outermost surfaces of the threads are disposed further from an axial center of the member than the conductive strips in the sequence.

5. The apparatus as in claim 1, wherein a first probe element of the multiple probe elements is operative to temporarily contact each of the conductive strips in the first sequence as the member moves along the axis.

6. An apparatus comprising:
a member extending along an axis;
multiple conductive strips disposed on a surface of the member, the multiple conductive strips spaced apart from each other in a sequence along the axis; and
a probe element, the probe element in communication with the multiple conductive strips in the sequence over time, the probe element operative to detect a position setting of the member via sensing presence of the conductive strips in the sequence over time;
wherein the probe element includes a first sensing element and a second sensing element, the apparatus further comprising:

a sensor circuit in communication with the first sensing element and the second sensing element, the sensor circuit operative to detect: i) first instances of time in which both the first sensing element and the second sensing element simultaneously contact a respective conductive strip in the sequence, and ii) second instances of time in which both the first sensing element and the second sensing element do not simultaneously contact a respective conductive strip in the sequence.

7. The apparatus as in claim 1 further comprising:
a monitor circuit operative to detect a linear position of the member along the axis with respect to the probe elements based on the probe elements detecting presence of the conductive strips in the first sequence and the conductive strips in the second sequence over time.

8. The apparatus as in claim 1, wherein the conductive strips in the second sequence are offset along the axis with respect to conductive strips in the first sequence.

9. The apparatus as in claim 1, wherein the conductive strips in the second sequence are offset along the axis with respect to the conductive strips in the first sequence; and
wherein the conductive strips in the third sequence are offset along the axis with respect to both the conductive strips in the second sequence and the conductive strips in the first sequence.

10. A method comprising:
receiving a member, the member extending along an axis;
affixing multiple conductive strips to a surface of the member, the multiple conductive strips spaced apart from each other and including a first sequence of first conductive strips and a second sequence of second conductive strips along the axis;
disposing a first probe element to be in communication with the first sequence of first conductive strips depending upon a position setting of the member over time;
disposing a second probe element to be in communication with the second sequence of second conductive strips depending upon a position setting of the member over time; and
the first conductive strips in the first sequence spaced apart from each other along the axis, the second conductive strips in the second sequence spaced apart from each other along the axis, the first probe element and the second probe element operative to detect the position setting of the member via sensing presence of the multiple conductive strips in the first sequence and the second sequence over time.

11. The method as in claim 10, wherein affixing the multiple conductive strips to the member includes:
disposing the multiple conductive strips in an orthogonal manner with respect to the axis of the member.

12. The method as in claim 10 further comprising:
disposing threads on the surface of the member, the threads spiraling on the surface about the member along the axis.

13. The method as in claim 12 further comprising:
disposing outermost surfaces of the threads to be further from an axial center of the member than the multiple conductive strips.

14. The method as in claim 10 further comprising:
disposing the first probe element and the second probe element with respect to the member in which the first probe element temporarily contacts each of the conductive strips in the first sequence and the second probe element temporarily contact each of the conductive strips in the second sequence as the member is moved along the axis with respect to the first probe element and the second probe element.

15. The method as in claim 10 further comprising:
via a sensor circuit in communication with the first probe element and a third probe element, detecting: i) first instances of time in which both the first probe element and the third probe element simultaneously contact a respective conductive strip in the first sequence, and ii) second instances of time in which both the first probe element and the third probe element do not simultaneously contact a respective conductive strip in the first sequence.

16. The method as in claim 10 further comprising:
detecting a linear position of the member along the axis with respect to the first probe element based on the first probe element detecting presence of the first conductive strips in the first sequence.

\* \* \* \* \*

UNITED STATES PATENT AND TRADEMARK OFFICE
CERTIFICATE OF CORRECTION

PATENT NO. : 12,390,599 B2  
APPLICATION NO. : 17/117842  
DATED : August 19, 2025  
INVENTOR(S) : Craig A. Armiento et al.

Page 1 of 1

It is certified that error appears in the above-identified patent and that said Letters Patent is hereby corrected as shown below:

In the Claims

Column 28, Line 22, replace "ber." with --ber,--

Signed and Sealed this  
Twenty-eighth Day of October, 2025

John A. Squires  
*Director of the United States Patent and Trademark Office*